United States Patent [19]
Tsien et al.

[11] Patent Number: 6,046,925
[45] Date of Patent: Apr. 4, 2000

[54] PHOTOCHROMIC FLUORESCENT PROTEINS AND OPTICAL MEMORY STORAGE DEVICES BASED ON FLUORESCENT PROTEINS

[75] Inventors: Roger Y. Tsien, La Jolla; Roger Heim, Cardiff by the Sea; Andrew B. Cubitt; Robert M. Dickson, both of San Diego; William E. Moerner, La Jolla, all of Calif.

[73] Assignee: The Regents of the University of California, Oakland, Calif.

[21] Appl. No.: 08/839,685

[22] Filed: Apr. 14, 1997

[51] Int. Cl.[7] .................................................. G11C 13/04
[52] U.S. Cl. .......................... 365/111; 365/110; 536/23.4
[58] Field of Search .................................... 365/111, 110; 250/458.1, 461.2; 252/301.16; 536/23.4

[56] References Cited

U.S. PATENT DOCUMENTS

| | | | |
|---|---|---|---|
| 4,471,470 | 9/1984 | Swainson | 365/127 |
| 5,325,324 | 6/1994 | Rentzepis | 365/127 |
| 5,491,084 | 2/1996 | Chalfie et al. | 435/189 |
| 5,625,048 | 4/1997 | Tsien et al. | 536/23.4 |
| 5,777,079 | 7/1998 | Tsien et al. | 530/350 |
| 5,804,387 | 9/1998 | Cormack et al. | 435/6 |

FOREIGN PATENT DOCUMENTS

| | | |
|---|---|---|
| WO 91/01305 | 2/1991 | WIPO . |
| WO 95/07463 | 3/1995 | WIPO . |
| WO 95/21191 | 8/1995 | WIPO . |
| WO 96/23810 | 8/1996 | WIPO . |
| WO 96/23898 | 8/1996 | WIPO . |
| WO 96/27027 | 9/1996 | WIPO . |
| WO 96/27675 | 9/1996 | WIPO . |
| WO 97/20078 | 12/1996 | WIPO . |
| WO 97/26333 | 1/1997 | WIPO . |
| WO 97/11094 | 3/1997 | WIPO . |
| WO 97/42320 | 5/1997 | WIPO . |
| WO 97/28261 | 8/1997 | WIPO . |
| WO 98/21355 | 11/1997 | WIPO . |
| WO 98/32879 | 1/1998 | WIPO . |

OTHER PUBLICATIONS

Baldwin et al., Biochemistry 29:5509–9915 (1990) "Cloning and Expression . . . the Yellow Fluorescent".

Betzig and Trautman Science 257 189–195 (1992) "Near–Field Optics . . . the Diffraction Limit."

Bregic et al., Proc. Natl. Acad. Sci. 94 2306–2311 (1997) "Structural basis for . . . green fluorescent protein."

Chalfie et al., Science 263:802–805 (1994) "green Fluorescent Protein as a Marker for Gene Expression."

Chattoraj et al Proc. Natl. Acad. Sci 93 8362–8367 (1996) "Ultra–fast excited . . . and proton transfer."

Cheng et al., Nature Biotechnology 14:606–609 (May, 1996) "Use of green . . . in mammalian cells."

Cody et al. Biochemistry 32:1212–1218 (1993) "chemical structure . . . green–Flourescent protein."

Cubitt et al., Trends in Biochem. Sci. 20:488–455 (1995) "Understanding improving and using green flourescent proteins."

Delagrave et al., Bio/Technology 13:151–154 (1995) "Red–Shifled Excitation Mutants of the green Fluorescent protein."

Deschamps et al., Protein Expression and Purification, 6:555–558 (1995) "Rapid Purification . . . an HPLC Size–Exclusion Columm."

Dickson et al., Science 274 966–969 (1996) "Three–Dimensional Imaging . . . Poly (acrylamide) gels."

(List continued on next page.)

*Primary Examiner*—David Nelms
*Assistant Examiner*—Hoai V. Ho
*Attorney, Agent, or Firm*—Fish & Richardson P.C.

[57] ABSTRACT

Photochromic fluorescent protein moiety having two or more stable states having excitation or emission spectra that are shifted from one wavelength region to another wavelength region in the two states are described. The photochromic material switches between states by irradiation with light of appropriate wavelengths. The two states are preferably stable at room temperature and in the dark. The switching between states can be reversible.

87 Claims, 9 Drawing Sheets

OTHER PUBLICATIONS

Dvornikov et al., J. Phys. Chem. 98 6746–6752 (1994) "Spectroscopy and Kinetics of Photochromic Materials for 3D Optical MD."

Ehrig et al., FEBS Letters 367:163–166 (1995) "green–fluorescent protein . . . excitation spectra."

Hanazawa et al J. Chem. Soc., Chem. Commun., 206–207 (1992) "Thermally Irreversible . . . Derivatives."

Heim et al., Proc. Natl. Acad. Sci. U.S.A. 91:12501–12505 (1994) "Wavelength mutation . . . green fluorescent protein."

Heim et al. Nature 373:663–664 (1995) "Anticipated Stimulis across skin."

Heim et al., Current Biology 6:178–182 (Feb. 1996) "Engineering green–fluorescent protein . . . energy transfer."

Irie and Mohri j. Org. Chem. 53 803–808 (1988) "Thermally Irreversible . . . Derivatives."

Kain et al. BioTechniques 19:650–655 (1995) "green Flourescent protein . . . protein localization."

Levine et al., Comp. Biochem. Physiol. 728:77–85 (1982) "Isolation and characterization . . . gregarium."

Mitra et al., Gene 173:13–17 (1996) "Flourescence resonance . . . the green fluorescent protein."

Moerner Science 265 46–53 (1994) "Examining Nanoenvironments . . . Isolated Impurity Molecule."

Muhlrad et al., Yeast 8:79–82 (1992) "A Rapid Method for a Localized Mutagenesis of Yeast genes."

Niwa et al proc. Natl. Acad. Sci 93 13617–13622 (1996) "Chemical nature of the light . . . green fluorescent protein."

Norris et al., Plant Molecular Biology, 24:673–677 (1994) "Nucleotide sequence . . . the dino flagellale symbiodinium."

Ormo et al., Science 273 1392–1395 (1996) "Crystal structure of the Aequourea victoria green flourescent protein."

Parthenopoulos and Rentzepis Science 245 843–845 (1989) "Three–dimensional Optical storage Memory."

Prasher et al., Gene 111:229–233 (1992) "Summary Structure of the Aequorea Victoria green fluorescent proteins."

Psaltis and Mok Scientific American Nov. 70–76 (1995) "Holigraphic Memories."

Terris et al., Appl. Phys. Lett. 68 141–143 (1996) "Near–field optical data storage."

Ward, in Bioluminescence and Chemiluminescence (eds. DeLuca et al., 235–242 (Academic Press, New York, 1981) "Properties of the Coelenterate green–fluorescent proteins."

Ward et al., Biochemistry 21:4535–4540 (1982) "Reversible Denaturation . . . the Renatured Protein."

Ward et al., Photochem. Photobiol. 35:803–808 (1982) "Spectral pertubation . . . green Fluorescent proteins."

Wilbanks et al., J. Biol. Chem. 268:1226–1235 (1993) "Rod structure of a phycoerythrin II—containing phycobilisome."

Yang et al., Nature Biotech. 14 1246–1251 (1996) "The molecular structure of green fluorescent protein."

Youvan and Michel–Beyerle nature Biotech 14 1219–1220 (1996) "Structure and fluorescence mechanism of GFP."

Yokoe and Meyer Nature Biotech 14 1252–1256 (1996) "Spatial dynamics . . . by local fluorescence enhancement."

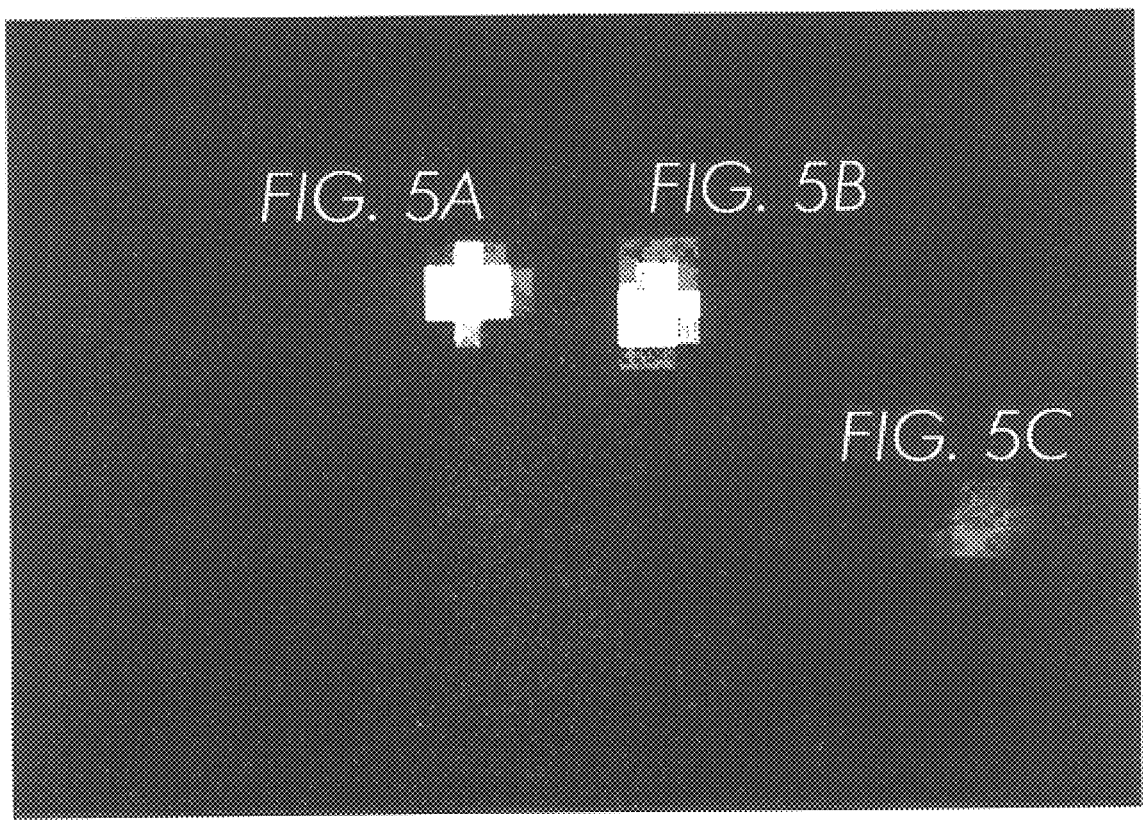
FIG. 5A  FIG. 5B
FIG. 5C
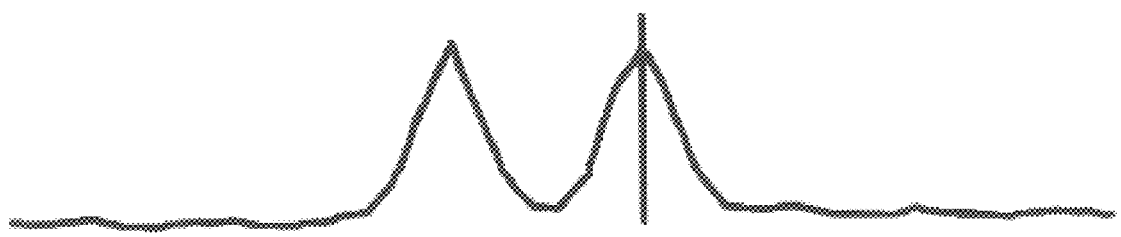
FIG. 5D

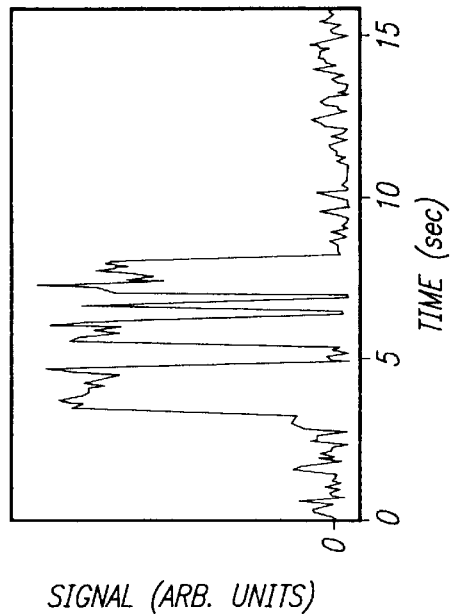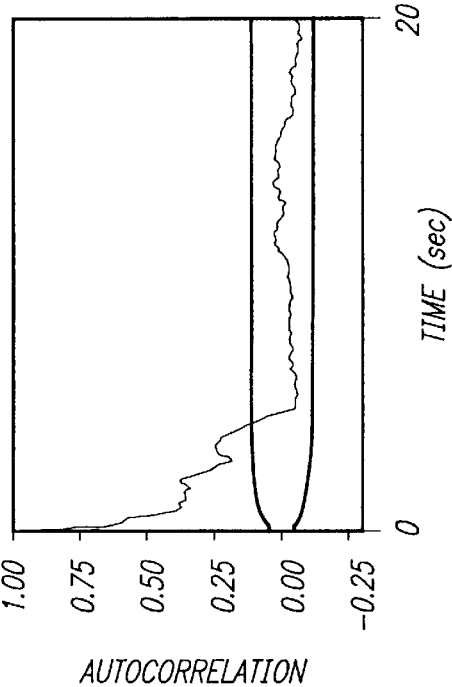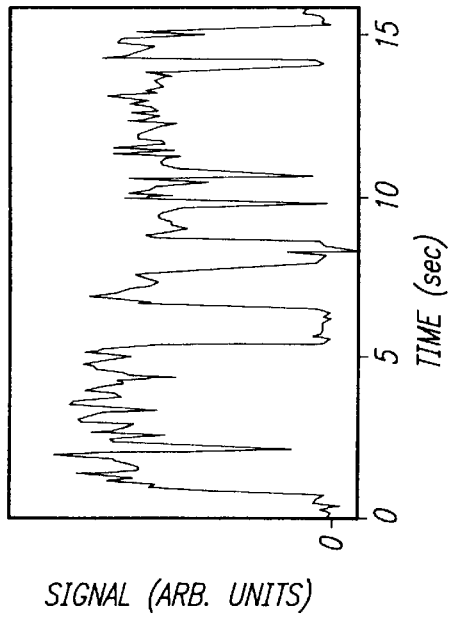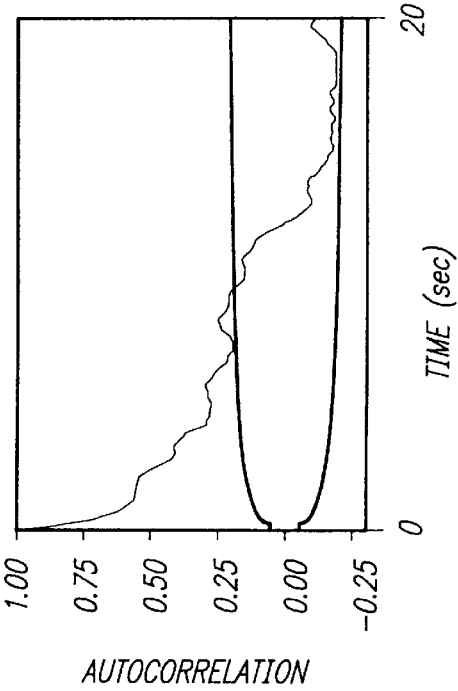

PHOTOCHROMIC FLUORESCENT PROTEINS AND OPTICAL MEMORY STORAGE DEVICES BASED ON FLUORESCENT PROTEINS

STATEMENT AS TO FEDERALLY SPONSORED RESEARCH

This invention was made with Government support under Grant No. DMR-9612252, awarded by the National Science Foundation. The Government has certain rights in this invention.

BACKGROUND OF THE INVENTION

The invention relates to optical memory devices using photochromic fluorescent protein moieties.

Photochromic materials can be used in a variety of applications, such as optical memory devices, described, for example, in Irie, M. & Mori, M. *J. Org. Chem.* 53:803 (1988); Parthenopoulos, D. A. & Rentzepis, P. M. *Science* 245:843 (1989); Hanazawa, M., et al. *J. Chem. Soc. Chem. Commun.* 206 (1992); Dvornikov, A. S., et al. *J. Phys. Chem.* 98:6746–6752 (1994); Dvornikov, A. S. & Rentzepis, P. M. *Opt. Mem. Neur. Netw.* 3:75–86 (1994); U.S. Pat. No. 4,471,470; and U.S. Pat. No. 5,325,324. The photochromic materials can be used in single-molecule optical storage at low temperatures. See, W. E. Moerner, *Science* 265:46 (1994). The photochromic materials have two states that are interconverted by irradiation. Optical devices based on bacteriorhodopsin (BR) are known, but do not allow for fluorescence detection.

The fluorescence behavior of wild-type (WT) green fluorescent protein (GFP) is known to have two absorption maxima, one at 395 nm, the other at 465 nm, but only one emission peak at 490 nm, indicating a common excited state. See, Heim, R., et al. *Proc. Nat. Acad. Sci., USA* 91:12501 (1994). The absorption peaks have been attributed to the neutral(state N) and anionic fluorophore states (state A⁻), respectively. The states can be interconverted by proton transfer between the fluorophore and Glu222. See, for example, Cubitt, A. B., et al. *Trends in Biochem. Sci.* 20:448 (1995); Chattoraj, M., et al. *Proc. Nat. Acad. Sci., USA* 93, 8362 (1996); and Brejc, K., et al. *Proc. Nat. Acad. Sci., USA* 94:2306–2311 (1997). Ser65 and Thr203 are particularly close to the chromophore in GFPs. See, Ormo, M., et al. *Science* 273:1392 (1996); Yang, F., et al. *Nature Biotech.* 14:1246 (1996). Consequently, these residues can strongly influence the photophysical properties of the protein. Alteration of Ser65 strongly favors ionization of the chromophore by hindering salvation and ionization of Glu222, whereas mutational loss of the Thr203 hydroxyl exerts a weaker opposing effect by reducing the salvation of the anionic form. See, Ormo, M., et al. *Science* 273:1392 (1996); Yang, F., et al. *Nature Biotech.* 14:1246 (1996). Aromatic residues at position 203 increase the peak excitation wavelength by 13–24 nm, probably by increasing the polarizability around the chromophore through p-p interactions. See, Ormo, M., et al. *Science* 273:1392 (1996).

In addition, new fluorescent proteins based on GFP have been identified by random screening of GFPs on plates. See, for example, Heim, R., et al. *Proc. Natl. Acad. Sci. USA* 91:12501–12504 (1994); Ehrig, et al. *FEBS Lett.* 367:163–166 (1995); and Delagrave, et al. *Bio/Technology* 13:151–154 (1995). In each case, the bacteria were transformed with GFP cDNA (containing a large number of different mutations) and spread onto agar plates following standard molecular biological methods such as described in chapter 1 of *Molecular Cloning, a Laboratory Manual*, 2nd ed., by J Sambrook, E. F. Fritsch & T. Maniatis, Cold Spring Harbor Laboratory Press (1989). The resulting bacterial colonies were illuminated first with one excitation wavelength (i.e., 390–395 nm) then another excitation wavelength (i.e., 470–475 nm). Colonies that showed any unusual emission color or difference in brightness between the two excitation wavelengths were picked up by a sterile wire loop and grown further. The procedure can be carried out either by the eye or by a digital imaging system on a computer. See, for example, Youvan, D. C., et al. *Methods in Enzymology*, 246:732–748 (1995).

SUMMARY OF THE INVENTION

The invention provides a photochromic fluorescent protein moiety having two or more stable states having excitation or emission spectra that are shifted from one wavelength region to another wavelength region in the two states. The photochromic material switches between states by irradiation with light of appropriate wavelengths. The two states are preferably stable at room temperature.

In one aspect, the invention features an optical memory device including a photochromic fluorescent protein moiety which is capable of being converted from a first state to a second state by irradiation with a writing wavelength. The first state has a first excitation wavelength maximum. A wavelength maximum is the wavelength in a spectrum which has the highest intensity absorbance or emission.

The first state and the second state are substantially stable at room temperature. A state is substantially stable at room temperature when it does not convert to another state in less than a second without irradiation. Substantially stable states can be last for periods of time ranging from minutes to days. The "first state" is the predominant state in which the photochromic fluorescent protein moiety is found in the natural state, when it is first isolated and prior to exposure to photochromic irradiation.

In another aspect, the invention features an optical memory device including an Aequorea-related photochromic fluorescent protein moiety which is capable of being converted from a first state to a second state by irradiation with a writing wavelength.

The optical memory device can further include a medium having a plurality of fluorescent protein moieties distributed throughout the medium. The medium can be configured as a planar surface or a volume. The medium can include polyacrylamide.

In preferred embodiments, each of the fluorescent protein moieties is individually addressable in the optical memory device.

In another aspect, the invention features a composition including a photochromic fluorescent protein moiety capable of being converted from a first state to a second state by irradiation with a writing wavelength. The first state has a first excitation wavelength maximum and the second state has a second excitation wavelength maximum. Excitation of the second state at the second excitation maximum can produce an intensity that is at least 4 times, preferably 8 times, and more preferably 10 times, greater than the intensity of the first state at the second excitation maximum. The first state and the second state are substantially stable at room temperature.

In another aspect, the invention features a method for storing and recovering information. The method includes the steps of: addressing a photochromic fluorescent protein moiety; exposing the photochromic fluorescent protein moiety to the writing wavelength; irradiating the photochromic fluorescent protein moiety with a reading wavelength; and detecting an output to determine whether the photochromic fluorescent protein moiety is in the first state or second state. The method can further include the step of exposing the photochromic fluorescent protein moiety with an erasing wavelength. The step of detecting the output can include measuring an emission wavelength.

In preferred embodiments, the photochromic fluorescent protein moiety is an Aequorea-related photochromic fluorescent protein moiety. The fluorescent protein moiety can include an amino acid substitution of T203 (e.g., T203F, T203Y, T203S, S65G/S72A/T203F, S65G/S72A/T203Y, or T203S/S205T). The photochromic fluorescent protein moiety can be a single polypeptide.

The photochromic fluorescent protein moiety can be capable of being converted from the second state to the first state by irradiation with an erasing wavelength. The second state can have a second excitation wavelength maximum which is longer than the first excitation wavelength maximum. Excitation of the second state at the second excitation maximum can produce an intensity that is at least 4 times, preferably 8 times, and more preferably 10 times, greater than the intensity of the first state at the second excitation maximum. In certain preferred embodiments, the second state has a second excitation wavelength maximum which is shorter than the first excitation wavelength maximum.

In another aspect, the invention features a method of improving the photochromic response of a fluorescent protein moiety. The method includes the first step of growing a plate of bacteria containing a large number of mutations that express a photochromic fluorescent protein moiety to provide a plurality of colonies. In the next step of the method, the colonies are exposed to a first excitation wavelength and measuring an intensity of a resulting first emission I(A1) from the exposure to the first excitation wavelength of a colony. The colonies are then exposed to a second excitation wavelength and measuring an intensity of a resulting second emission I(B1) from the exposure to the second excitation wavelength of a colony. The colonies are exposed to an isomerization wavelength, after which the colonies are exposed to the first excitation wavelength and measuring an intensity of a first emission I(A2) from the exposure to the first excitation wavelength for a colony and to the second excitation wavelength and measuring an intensity of a second emission I(B2) from the exposure to the second excitation wavelength for a colony. The ratios of emission intensities are determined from the colony before and after exposure to the isomerization wavelength. The colony or colonies having improved photochromic response of the photochromic fluorescent protein moiety are selected if the ratio of emission intensities is substantially different from an average ratio of emission intensities for the plurality of colonies.

The determining step can include calculating the ratio I(A2)/I(A1), I(B2)/I(B1), or I(A2)I(B1)/I(A1)I(B2). The method can include exposing the plurality of colonies to an initial wavelength prior to the first exposing and measuring step. The exposing and measuring steps can be performed with a digital imaging system. The method can include picking up (e.g., robotically) a portion of the colony having improved photochromic response of the photochromic fluorescent protein moiety.

In another aspect, the invention features an isolated nucleic acid sequence which encodes the photochromic fluorescent protein moiety. The nucleic acid sequence can be contained in an expression vector.

In another aspect, the invention features an expression vector including expression control sequences operatively linked to a nucleic acid sequence coding for the expression of the photochromic fluorescent protein moiety. The expression vector can be adapted for function in a prokaryotic cell or a eukaryotic cell. In another aspect, the invention features a host cell transfected with the expression vector. The host cell can be a prokaryote (e.g., *E. coli*), or a eukaryotic cell, such as a yeast cell, or a mammalian cell.

"Fluorescent protein" refers to any protein capable of emitting light when excited with appropriate electromagnetic radiation. Fluorescent proteins include proteins having amino acid sequences that are either natural or engineered, such as the fluorescent proteins derived from Aequorea-related fluorescent proteins. A fluorescent protein is an Aequorea-related fluorescent protein if any contiguous sequence of 150 amino acids of the fluorescent protein has at least 85% sequence identity with an amino acid sequence, either contiguous or non-contiguous, from the wild type Aeguorea green fluorescent protein. More preferably, a fluorescent protein is an Aequorea-related fluorescent protein if any contiguous sequence of 200 amino acids of the fluorescent protein has at least 95% sequence identity with an amino acid sequence, either contiguous or non-contiguous, from the wild type Aequorea green fluorescent protein.

"Moiety" refers to a radical of a molecule that is attached to another radical of the indicator. Thus, a "fluorescent protein moiety" is the radical of a fluorescent protein coupled to another radical, such as a hydrogen radical, another functional moiety, or another protein moiety.

"Peptide" refers to a polymer in which the monomers are amino acid residues which are joined together through amide bonds, alternatively referred to as a polypeptide. A "single polypeptide" is a continuous peptide that constitutes the protein without non-amino acid spacers. When the amino acids are alpha-amino acids, either the L-optical isomer or the D-optical isomer can be used, the L-isomers being preferred. Additionally, unnatural amino acids such as beta-alanine, phenylglycine, and homoarginine are meant to be included. Commonly encountered amino acids which are not gene-encoded can also be used in the present invention, although preferred amino acids are those that are encodable. For a general review, see, for example, Spatola, A. F., in *Chemistry and Biochemistry of Amino Acids, Peptides and Proteins*, B. Weinstein, ed., Marcel Dekker, New York, p. 267 (1983).

"Operatively linked" refers to a juxtaposition wherein the components so described are in a relationship permitting them to function in their intended manner. A control sequence operatively linked to a coding sequence is ligated such that expression of the coding sequence is achieved under conditions compatible with the control sequences. "Control sequence" refers to polynucleotide sequences which are necessary to effect the expression of coding and non-coding sequences to which they are ligated. Control sequences generally include promoter, ribosomal binding site, and transcription termination sequence. The term "control sequences" is intended to include, at a minimum, components whose presence can influence expression, and can also include additional components whose presence is advantageous, for example, leader sequences and fusion partner sequences.

"Polynucleotide" refers to a polymeric form of nucleotides of at least 10 bases in length. The nucleotides can be ribonucleotides, deoxynucleotides, or modified forms of either type of nucleotide. The term includes single and double stranded forms of DNA.

The photochromic fluorescent protein moieties can be immobilized in a gel matrix (i.e. PAA). The single-molecule spectroscopic data on the photochromic fluorescent protein moieties based on GFP indicate that: (a) the long-wavelength anionic state emission eventually disappears; and (b) the anionic state can be regenerated by direct irradiation of the neutral state at 405 nm. By interfering with the hydrogen bonding network and affecting the polarity of the immediate salvation shell, T203Y and T203F exhibit distinct, but interconvertable neutral and anionic states with very different photophysical properties, both markedly different from the WT photophysics.

Imaging of wild-type GFP in whole cells typically requires many thousands of copies/cell. See, for example, Niswender, K. D., et al. *J. Microsc.* 180:109 (1995). In contrast, the combination of intense laser excitation, lack of autofluorescence from pure PAA, reduction of illuminated volume in total internal reflection, and utilization of improved GFPs with an extremely sensitive detector enables detection of individual molecules. The on/off behavior of the single GFP molecule intensity versus time is reminiscent of typical recordings of current through single ion channels. See, Sakmann, B. & Neher, E. (Plenum Press, New York, 1995). Due to available recombinant techniques, it is possible to mutate and screen other GFP varieties to facilitate or suppress the switching behavior.

Although irreversible photodestruction can occur eventually, most of the photochromic fluorescent protein moieties emit several millions of photons without harm. For GFP and its variants, this is true even though the aqueous air-saturated environment contains plenty of oxygen, which usually destroys fluorophores. For comparison, fluorescein only emits on average $\leq 4 \times 10^4$ photons per molecule before bleaching. See, for example, Tsien, R. Y. & Waggoner, A. in *Handbook of Biological Confocal Microscopy* 2nd ed. (ed. Pawley, J. B.) pp. 267–279, Plenum Press, New York, (1995). The resistance of the GFPs to photodestruction is probably due to the complete encapsulation of the fluorophore inside a rigid β-barrel. See, Ormo, M., et al. *Science* 273:1392 (1996); and Yang, F., et al. *Nature Biotech.* 14:1246 (1996).

The photochromic fluorescent protein moieties have accessible states that are stable at room temperature, making it possible to construct single-molecule optical storage devices that can operate at room temperature. Furthermore, by using near-field optics, individual molecules can be addressed as a bit on a planar surface. High density storage media can be achieved.

Other features or advantages of the present invention will be apparent from the following detailed description of the invention, and also from the claims.

BRIEF DESCRIPTION OF THE DRAWINGS

FIGS. 5A–5C is an image of fluorescence emission from three single GFP molecules.

FIG. 5D is a graph depicting a line intensity profile at the position of the arrow.

FIGS. 6A and 6B are graphs depicting fluorescence intensity versus time traces for T203Y (FIG. 6A) and T203F (FIG. 6B).

FIGS. 6C and 6D are graphs depicting autocorrelations of the fluorescence trajectories A and B expanded to illustrate the decay over the first 20 seconds are presented in C and D, respectively, with confidence limits.

DETAILED DESCRIPTION

The wild-type (WT) Green Fluorescent Protein (GFP) from the jellyfish *Aequorea Victoria* can be mutated to produce new proteins and protein fragments (i.e., protein moieties) that are photochromic. A photochromic fluorescent protein moiety is a protein that has more than one stable state having different spectral properties. Each state has excitation or emission spectra that are shifted from one wavelength region to another wavelength region in the two states. A photochromic material switches between states by irradiation with light of appropriate wavelengths. The switching between states can be reversible. The two states are preferably stable at room temperature and in the dark.

Figure 1:
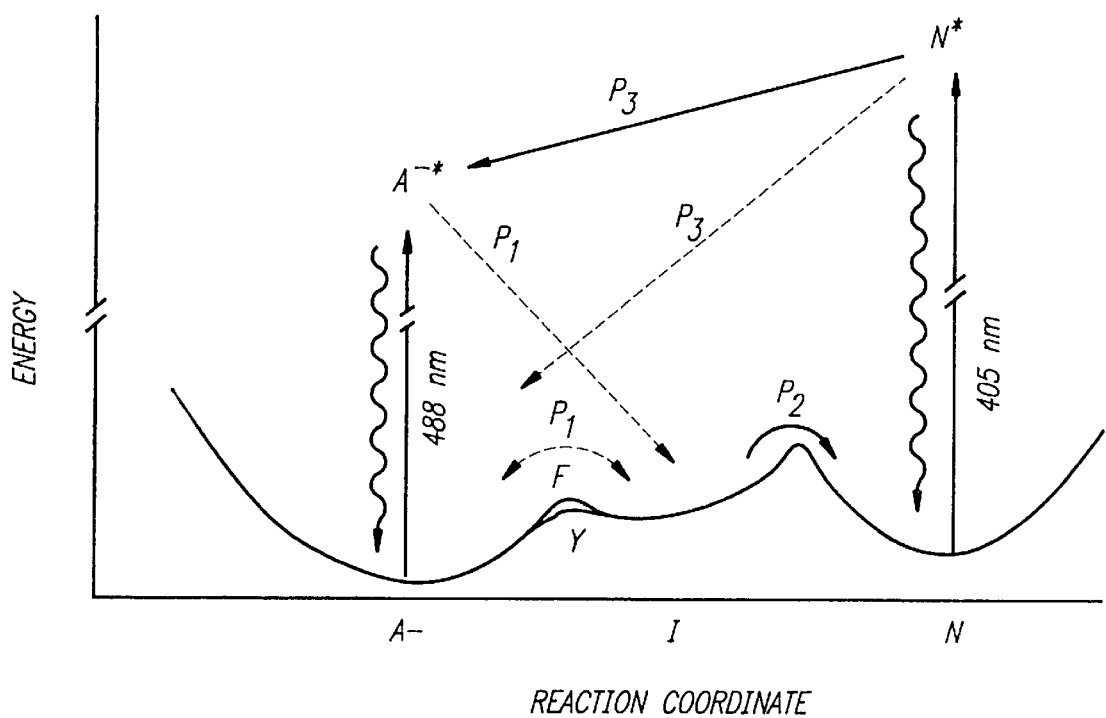
FIG. 1 is a schematic diagram of accessible states for a photochromic fluorescent protein moiety.

For example, referring to FIG. 1, the photochromic fluorescent protein moiety can excited by light of appropriate intensity within the excitation spectrum (i.e., 488 nm) of the fluorophore in state A⁻ ($\lambda_{excitation}$). The excited state fluorophore in state A⁻ emits energy as fluorescent light ($\lambda_{emission\ 1}$). The photochromic fluorescent protein moiety can be switched to another stable state (e.g., state N) by further irradiation. State N can be excited by light at a different excitation wavelength (e.g., $\lambda_{excitation\ 2}$).

The degree of photochromism can be determined by any change in spectral characteristic of the fluorescent protein moiety. Preferably, photochromic behavior can be identified by monitoring changes in the excitation spectrum, which are determined as a function of the change in the ratio of excitation intensities from the different states of the photochromic fluorescent protein moiety at a particular wavelength. A more detailed analysis of the photochromism can be accomplished by monitoring the change in the excitation intensity at more than one wavelength.

Fluorescence in a sample can be measured using a fluorometer. In general, excitation radiation, from an excitation source having a first wavelength, passes through excitation optics. The excitation optics cause the excitation radiation to excite the sample. In response, fluorophores in the sample emit radiation which has a wavelength that is different from the excitation wavelength. Collection optics then collect the emission from the sample. The device can include a temperature controller to maintain the sample at a specific temperature while it is being scanned. The device can also include a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

Methods of determining the properties of fluorescent materials are well known in the art and are described in, e.g., Lakowicz, J. R., *Principles of Fluorescence Spectroscopy*, New York:Plenum Press (1983); Herman, B., Resonance energy transfer microscopy, in: *Fluorescence Microscopy of Living Cells in Culture*, Part B, *Methods in Cell Biology*, vol. 30, ed. Taylor, D. L. & Wang, Y. -L., San Diego: Academic Press (1989), pp. 219–243; Turro, N. J., *Modern Molecular Photochemistry*, Menlo Park: Benjamin/Cummings Publishing Col, Inc. (1978), pp. 296–361. The excited state lifetime and quantum yields can be determined. For example, quantum yields of wild-type GFP, S65T, and P4-1 mutants can be estimated by comparison with fluorescein in 0.1N NaOH as a standard of quantum yield 0.91 and mutants P4 and P4-3 can be compared to 9-aminoacridine in water (quantum yield 0.98). The method is described, for example, in J. N. Miller, ed., *Standards in Fluorescence Spectrometry*, New York: Chapman and Hall (1981).

It is desirable for the photochromic fluorescent protein moiety to have a high fluorescence quantum yield and a high degree of reversibility of the photoconversion between states.

Green fluorescent proteins of cnidarians, which act as their energy-transfer acceptors in bioluminescence, are suitable fluorescent proteins for use in the photochromic fluorescent protein moieties. A green fluorescent protein ("GFP") is a protein that emits green light, and a blue fluorescent protein ("BFP") is a protein that emits blue light. GFPs have been isolated from the Pacific Northwest jellyfish, *Aequorea victoria*, the sea pansy, *Renilla reniformis*, and *Phialidium gregarium*. See, Ward, W. W., et al., *Photochem. Photobiol.*, 35:803–808 (1982); and Levine, L. D., et al., *Comp. Biochem. Physiol.*, 72B:77–85 (1982).

A variety of Aequorea-related GFPs having useful excitation and emission spectra have been engineered by modifying the amino acid sequence of a naturally occurring GFP from *Aequorea victoria*. See, Prasher, D. C., et al., *Gene*, 111:229–233 (1992); Heim, R., et al., *Proc. Natl. Acad. Sci., USA*, 91:12501–04 (1994); U.S. Ser. No. 08/337,915, filed Nov. 10, 1994; International application PCT/US95/14692, filed Nov. 10, 1995; and U.S. Ser. No. 08/706,408, filed Aug. 30, 1996. The cDNA of GFP can be concatenated with those encoding many other proteins; the resulting fusions often are fluorescent and retain the biochemical features of the partner proteins. See, Cubitt, A. B., et al., *Trends in Biochem. Sci.* 20:448–455 (1995). Mutagenesis studies have produced GFP mutants with shifted wavelengths of excitation or emission. See, Heim, R. & Tsien, R. Y. *Current Biol.* 6:178–182 (1996); and Tsien, R. Y., et al., *Trends Cell Biol.* 3:242–245 (1993). Similarly, the fluorescent protein can be related to Renilla or Phialidium wild-type fluorescent proteins using the same standards. Some Aequorea-related engineered versions described in Table I. Other variants or mutants are within the scope of the invention as described, for example, in the Examples.

TABLE I

| Clone | Mutation(s) | Excitation max (nm) | Emission max (nm) | Extinction Coefficient ($M^{-1}cm^{-1}$) | Quantum yield |
|---|---|---|---|---|---|
| Wild type | none | 395 (475) | 508 | 21,000 (7,150) | 0.77 |
| P4 | Y66H | 383 | 447 | 13,500 | 0.21 |
| P4-3 | Y66H;Y145F | 381 | 445 | 14,000 | 0.38 |
| W7 | Y66W;N146I M153T V163A N212K | 433 (453) | 475 (501) | 18,000 (17,100) | 0.67 |
| W2 | Y66W;I123V Y145H H148R M153T V163A N212K | 432 (453) | 480 | 10,000 (9,600) | 0.72 |
| S65T | S65T | 489 | 511 | 39,200 | 0.68 |
| P4-1 | S65T;M153A K238E | 504 (396) | 514 | 14,500 (8,600) | 0.53 |
| S65A | S65A | 471 | 504 | | |
| S65C | S65C | 479 | 507 | | |
| S65L | S65L | 484 | 510 | | |
| Y66F | Y66F | 360 | 442 | | |
| Y66W | Y66W | 458 | 480 | | |
| 10c | S65G;V68L S72A;T203Y | 513 | 527 | | |
| W1B | F64L;S65T Y66W;N146I M153T V163A N212K | 432 (453) | 476 (503) | | |

TABLE I-continued

| Clone | Mutation(s) | Excitation max (nm) | Emission max (nm) | Extinction Coefficient (M$^{-1}$cm$^{-1}$) | Quantum yield |
|---|---|---|---|---|---|
| Emerald | S65T;S72A N149K M153T I167T | 487 | 508 | | |
| Sapphire | S72A;Y145F T203I | 395 | 511 | | |

An additional clone, W1B1, includes the following mutations: F64L; S65T; Y66W; F99S; and V163A.

Additional mutations in Aequorea-related fluorescent proteins, referred to as "folding mutations," improve the ability of fluorescent proteins to fold at higher temperatures and to be more fluorescent when expressed in mammalian cells, but have little or no effect on the peak wavelengths of excitation and emission. It should be noted that these may be combined with mutations that influence the spectral properties of GFP to produce proteins with altered spectral and folding properties. Folding mutations include: F64L, V68L, S72A, and also T44A, F99S, Y145F, N146I, M153T or A, V163A, I167T, S175G, S205T and N212K.

The photochromic fluorescent protein moieties can be produced as components of fusion proteins by recombinant DNA technology. See, for example, U.S. Ser. No. 08/706,408, filed Aug. 30, 1996. Recombinant production of photochromic fluorescent protein moieties involves expressing nucleic acids having sequences that encode the proteins. Nucleic acids encoding fluorescent proteins can be obtained by methods known in the art. For example, a nucleic acid encoding the known in the art. For example, a nucleic acid encoding the protein can be isolated by polymerase chain reaction of cDNA from *A. victoria* using primers based on the DNA sequence of *A. victoria* green fluorescent protein. PCR methods are described in, for example, U.S. Pat. No. 4,683,195; Mullis, et al. *Cold Spring Harbor Symp. Quant. Biol.* 51:263 (1987), and Erlich, ed., *PCR Technology*, (Stockton Press, NY, 1989). The nucleic acid can encode a fusion protein in which a single polypeptide includes the fluorescent protein moiety within a longer polypeptide.

Mutant versions of photochromic fluorescent proteins can be made by site-specific mutagenesis of other nucleic acids encoding fluorescent proteins, or by random mutagenesis caused by increasing the error rate of PCR of the original polynucleotide with 0.1 mM MnCl$_2$ and unbalanced nucleotide concentrations. See, e.g., U.S. patent application Ser. No. 08/337,915, filed Nov. 10, 1994 or International application PCT/US95/14692, filed Nov. 10, 1995.

The construction of expression vectors and the expression of genes in transfected cells involves the use of molecular cloning techniques also well known in the art. Sambrook et al., *Molecular Cloning—A Laboratory Manual*, Cold Spring Harbor Laboratory, Cold Spring Harbor, N.Y., (1989) and *Current Protocols in Molecular Biology*, F. M. Ausubel et al., eds., (Current Protocols, a joint venture between Greene Publishing Associates, Inc. and John Wiley & Sons, Inc., most recent Supplement).

Nucleic acids used to transfect cells with sequences coding for expression of the polypeptide of interest generally will be in the form of an expression vector including expression control sequences operatively linked to a nucleotide sequence coding for expression of the polypeptide. As used, the term "nucleotide sequence coding for expression of" a polypeptide refers to a sequence that, upon transcription and translation of mRNA, produces the polypeptide. This can include sequences containing, e.g., introns. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons.

Methods which are well known to those skilled in the art can be used to construct expression vectors containing the photochromic fluorescent protein moieties coding sequence and appropriate transcriptional/translational control signals. These methods include in vitro recombinant DNA techniques, synthetic techniques and in vivo recombination/genetic recombination. (See, for example, the techniques described in Maniatis, et al., *Molecular Cloning A Laboratory Manual*, Cold Spring Harbor Laboratory, N.Y., 1989).

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the CaCl$_2$ method by procedures well known in the art. Alternatively, MgCl$_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransfected with DNA sequences encoding the fusion polypeptide of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukaryotic Viral Vectors*, Cold Spring Harbor Laboratory, Gluzman ed., 1982). Preferably, a eukaryotic host is utilized as the host cell as described herein.

Techniques for the isolation and purification of either microbially or eukaryotically expressed polypeptides of the invention may be by any conventional means such as, for example, preparative chromatographic separations and immunological separations such as those involving the use of monoclonal or polyclonal antibodies or antigen.

A variety of host-expression vector systems may be utilized to express the photochromic fluorescent protein moiety coding sequence. These include but are not limited to microorganisms such as bacteria transformed with recombinant bacteriophage DNA, plasmid DNA or cosmid DNA expression vectors containing a photochromic fluorescent protein moiety coding sequence; yeast transformed with recombinant yeast expression vectors containing the photochromic fluorescent protein moiety coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a photochromic fluorescent protein moiety coding sequence; insect cell systems infected with recombinant virus expression vectors (e.g., baculovirus) containing a photochromic fluorescent protein moiety coding sequence; or animal cell systems infected with recombinant virus expression vectors (e.g., retroviruses, adenovirus, vaccinia virus) containing a photochromic fluorescent protein moiety coding sequence, or transformed animal cell systems engineered for stable expression.

Depending on the host/vector system utilized, any of a number of suitable transcription and translation elements, including constitutive and inducible promoters, transcription enhancer elements, transcription terminators, etc. may be used in the expression vector (see, e.g., Bitter, et al., Methods in Enzymology 153:516–544, 1987). For example, when cloning in bacterial systems, inducible promoters such as pL of bacteriophage $\lambda$, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted photochromic fluorescent protein moiety coding sequence.

In bacterial systems a number of expression vectors may be advantageously selected depending upon the use intended for the photochromic fluorescent protein moiety expressed. For example, when large quantities of the photochromic fluorescent protein moiety are to be produced, vectors which direct the expression of high levels of fusion protein products that are readily purified may be desirable. Those which are engineered to contain a cleavage site to aid in recovering photochromic fluorescent protein moieties are preferred.

In yeast, a number of vectors containing constitutive or inducible promoters may be used. For a review see, Current Protocols in Molecular Biology, Vol. 2, Ed. Ausubel, et al., Greene Publish. Assoc. & Wiley Interscience, Ch. 13, 1988; Grant, et al., Expression and Secretion Vectors for Yeast, in Methods in Enzymology, Eds. Wu & Grossman, 31987, Acad. Press, N.Y., Vol. 153, pp.516–544, 1987; Glover, DNA Cloning, Vol. II, IRL Press, Wash., D.C., Ch. 3, 1986; and Bitter, Heterologous Gene Expression in Yeast, Methods in Enzymology, Eds. Berger & Kimmel, Acad. Press, N.Y., Vol. 152, pp. 673–684, 1987; and The Molecular Biology of the Yeast Saccharomyces, Eds. Strathern et al., Cold Spring Harbor Press, Vols. I and II, 1982. A constitutive yeast promoter such as ADH or LEU2 or an inducible promoter such as GAL may be used (Cloning in Yeast, Ch. 3, R. Rothstein In: DNA Cloning Vol.11, A Practical Approach, Ed. D. M. Glover, IRL Press, Wash., D.C., 1986). Alternatively, vectors may be used which promote integration of foreign DNA sequences into the yeast chromosome.

In cases where plant expression vectors are used, the expression of a photochromic fluorescent protein moiety coding sequence may be driven by any of a number of promoters. For example, viral promoters such as the 35S RNA and 19S RNA promoters of CaMV (Brisson, et al., Nature 310:511–514, 1984), or the coat protein promoter to TMV (Takamatsu, et al., EMBO J. 6:307–311, 1987) may be used; alternatively, plant promoters such as the small subunit of RUBISCO (Coruzzi, et al., 1984, EMBO J. 3:1671–1680; Broglie, et al., Science 224:838–843, 1984); or heat shock promoters, e.g., soybean hsp17.5-E or hsp17.3-B (Gurley, et al., Mol. Cell. Biol. 6:559–565, 1986) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, Methods for Plant Molecular Biology, Academic Press, NY, Section VIII, pp. 421–463, 1988; and Grierson & Corey, Plant Molecular Biology, 2d Ed., Blackie, London, Ch. 7–9, 1988.

An alternative expression system which could be used to express a photochromic fluorescent protein moiety is an insect system. In one such system, Autographa californica nuclear polyhedrosis virus (AcNPV) is used as a vector to express foreign genes. The virus grows in Spodoptera frugiperda cells. The photochromic fluorescent protein moiety coding sequence may be cloned into non-essential regions (for example, the polyhedrin gene) of the virus and placed under control of an AcNPV promoter (for example the polyhedrin promoter). Successful insertion of the photochromic fluorescent protein moiety coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed, see Smith, et al., J. Viol. 46:584, 1983; Smith, U.S. Pat. No. 4,215,051.

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and, advantageously secretion of the gene product should be used as host cells for the expression of a photochromic fluorescent protein moiety. Such host cell lines may include but are not limited to CHO, VERO, BHK, HeLa, COS, MDCK, Jurkat, HEK-293, and WI38.

Mammalian cell systems which utilize recombinant viruses or viral elements to direct expression may be engineered. For example, when using adenovirus expression vectors, the photochromic fluorescent protein moiety coding sequence may be ligated to an adenovirus transcription/ translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the photochromic fluorescent protein moiety in infected hosts (e.g., see Logan & Shenk, Proc. Natl. Acad. Sci. USA, 81:3655–3659, 1984). Alternatively, the vaccinia virus 7.5K promoter may be used. (e.g., see, Mackett, et al., Proc. Natl. Acad. Sci. USA,79:7415–7419, 1982; Mackett, et al., J.

Virol. 49:857–864, 1984; Panicali, et al., *Proc. Natl. Acad. Sci. USA* 79:4927–4931, 1982). Of particular interest are vectors based on bovine papilloma virus which have the ability to replicate as extrachromosomal elements (Sarver, et al., *Mol. Cell. Biol.* 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the photochromic fluorescent protein moiety gene in host cells (Cone & Mulligan, *Proc. Natl. Acad. Sci. USA,* 81:6349–6353, 1984). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with the photochromic fluorescent protein moiety cDNA controlled by appropriate expression control elements (e.g., promoter, enhancer, sequences, transcription terminators, poly-adenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including but not limited to the herpes simplex virus thymidine kinase (Wigler, et al., *Cell,* 11:223, 1977), hypoxanthine-guanine phosphoribosyltransferase (Szybalska & Szybalski, *Proc. Natl. Acad. Sci. USA,* 48:2026, 1962), and adenine phosphoribosyltransferase (Lowy, et al., *Cell,* 22:817, 1980) genes can be employed in tk$^{31}$, hgprt$^-$ or aprt$^-$ cells respectively. Also, antimetabolite resistance can be used as the basis of selection for dhfr, which confers resistance to methotrexate (Wigler, et al., *Proc. Natl. Acad. Sci. USA,* 77:3567, 1980; O'Hare, et al., *Proc. Natl. Acad. Sci. USA,* 8:1527, 1981); gpt, which confers resistance to mycophenolic acid (Mulligan & Berg, *Proc. Natl. Acad. Sci. USA,* 78:2072, 1981; neo, which confers resistance to the aminoglycoside G-418 (Colberre-Garapin, et al., *J. Mol. Biol.,* 150:1, 1981); and hygro, which confers resistance to hygromycin (Santerre, et al., *Gene,* 30:147, 1984) genes. Recently, additional selectable genes have been described, namely trpB, which allows cells to utilize indole in place of tryptophan; hisD, which allows cells to utilize histinol in place of histidine (Hartman & Mulligan, *Proc. Natl. Acad. Sci. USA,* 85:8047, 1988); and ODC (ornithine decarboxylase) which confers resistance to the ornithine decarboxylase inhibitor, 2-(difluoromethyl)-DL-ornithine, DFMO (McConlogue L., In: *Current Communications in Molecular Biology,* Cold Spring Harbor Laboratory, ed., 1987).

DNA sequences encoding the photochromic fluorescent protein moiety polypeptide of the invention can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, in other words when the foreign DNA is continuously maintained in the host, are known in the art.

Recombinant photochromic fluorescent protein moiety can be produced by expression of nucleic acid encoding the protein in prokaryotes, such as *E. coli* or in eukaryotes, such as yeast cells or mammalian cells. The fluorophore of Aequorea-related photochromic fluorescent protein moiety results from cyclization and oxidation of residues 65–67.

The construct can also contain a tag to simplify isolation of the photochromic fluorescent protein moiety. For example, a polyhistidine tag of, e.g., six histidine residues, can be incorporated at the amino terminal end of the photochromic fluorescent protein moiety. The polyhistidine tag allows convenient isolation of the protein in a single step by nickel-chelate chromatography.

In a preferred embodiment, the photochromic fluorescent protein moiety is a fusion protein produced by recombinant DNA technology. The invention also envisions fusion proteins that contain extra amino acid sequences at the amino and/or carboxy termini, for example, polyhistidine tags.

Thus, photochromic fluorescent protein moieties encoded by a recombinant nucleic acid include sequences coding for expression of a photochromic fluorescent protein moiety. The recombinant nucleic acid can be incorporated into an expression vector comprising expression control sequences operatively linked to the recombinant nucleic acid. The expression vector can be adapted for function in prokaryotes or eukaryotes by inclusion of appropriate promoters, replication sequences, markers, etc.

The expression vector can be transfected into a host cell for expression of the recombinant nucleic acid. Host cells can be selected for high levels of expression in order to purify the photochromic fluorescent protein moiety fusion protein. *E. coli* is useful for this purpose. Alternatively, the host cell can be a prokaryotic or eukaryotic cell selected to study the activity of an enzyme produced by the cell. In this case, the linker peptide is selected to include an amino acid sequence recognized by the protease. The cell can be, e.g., a cultured cell or a cell in vivo.

A primary advantage of photochromic fluorescent protein moiety fusion proteins is that they are prepared by normal protein biosynthesis, thus completely avoiding organic synthesis and the requirement for customized unnatural amino acid analogs. The constructs can be expressed in *E. coli* in large scale for in vitro assays. Purification from bacteria is simplified when the sequences include polyhistidine tags for one-step purification by nickel-chelate chromatography. Alternatively, the substrates can be expressed directly in a desired host cell for assays in situ.

Without further elaboration, it is believed that one skilled in the art can, based on the description herein, utilize the present invention to its fullest extent. All patents and publications cited herein are hereby incorporated by reference.

Figure 2:
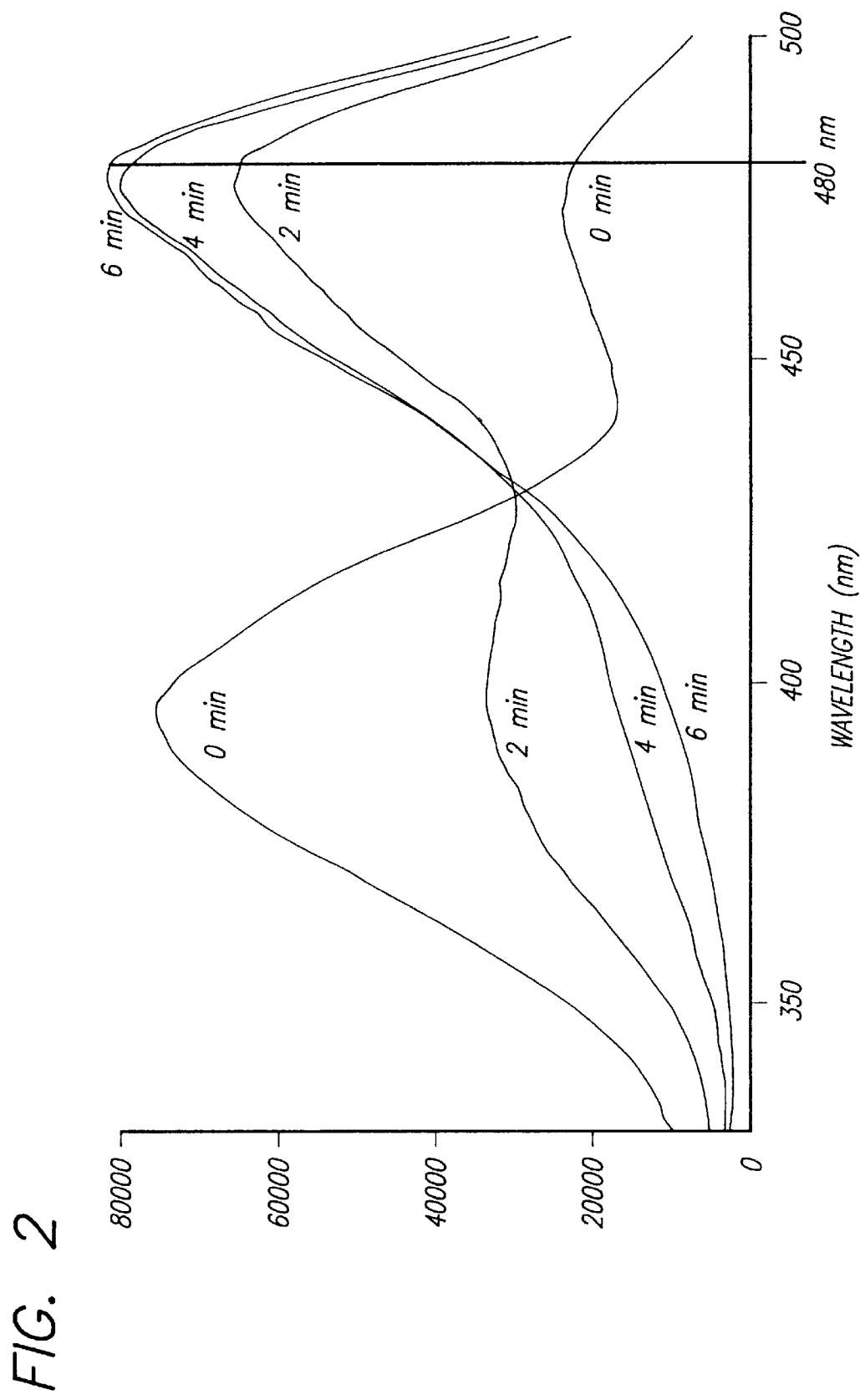
FIG. 2 is a graph depicting the excitation spectra of purified wild-type GFP as a function of exposure time to 254 nm irradiation.

Referring to FIG. 2, the excitation spectra of purified wild-type GFP as a function of exposure to 254 nm irradiation indicates photochromic behavior of the GFP. Fluorescence emission was collected up to 510 nm. The photoconversion between states was accomplished by irradiation with light at 254 nm. The initial spectrum taken before any exposure to 254 nm, labeled "0 min", shows the major excitation peak at 395 nm and a small minor peak at 475–480 nm. After 2, 4, and 6 minutes of irradiation at 254 nm, the 395 nm peak is progressively suppressed and the 475 nm peak is enhanced. The small difference between the 4 minute and 6 minute spectra indicate that the response has essentially reached completion by 6 minutes. The 480 nm excitation of the 0 minute spectrum is enhanced by a factor of 3.6 in 6 minute excitation spectrum.

Figure 3:
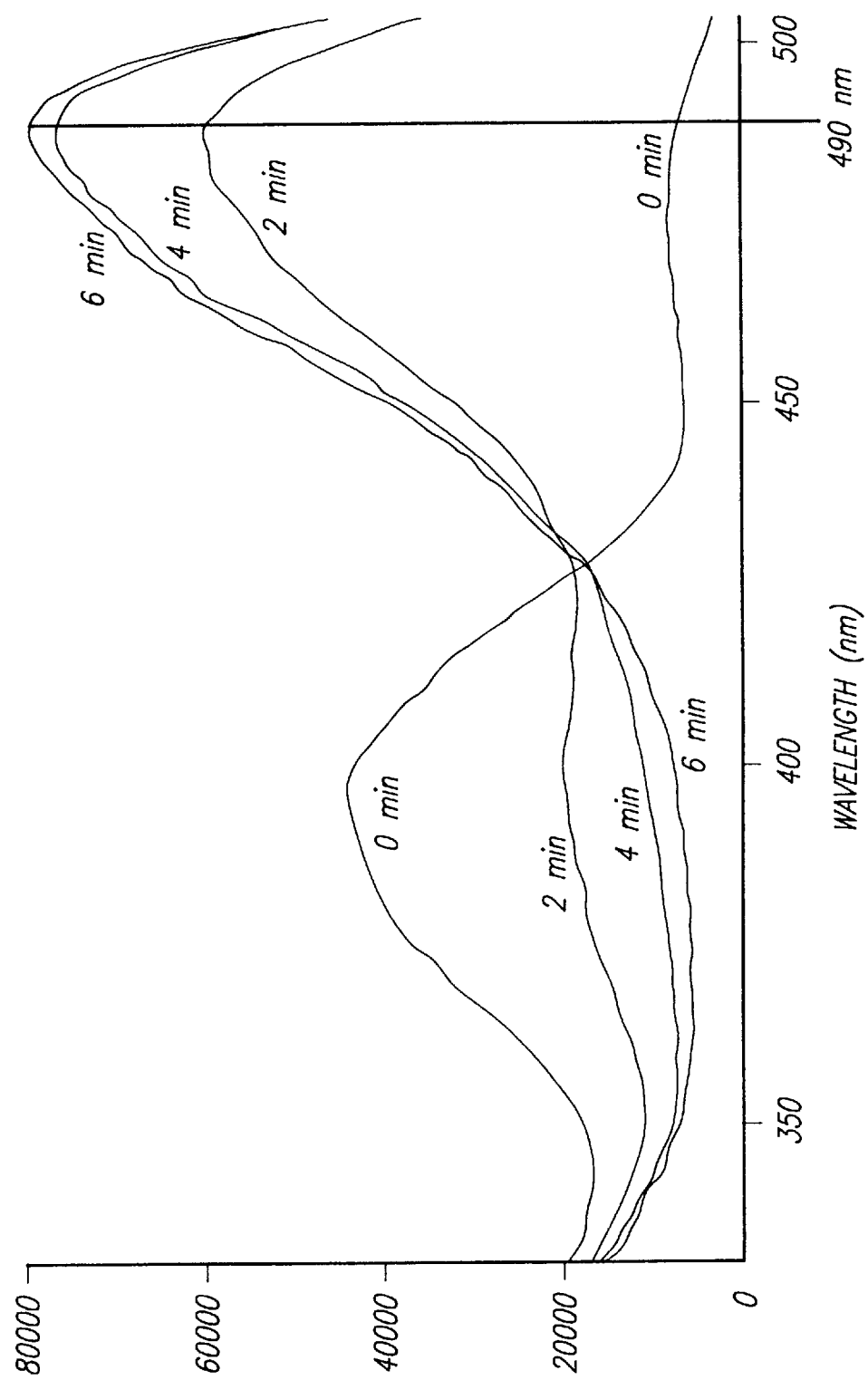
FIG. 3 is a graph depicting the excitation spectra of purified GFP with the mutations T203S and S205T as a function of exposure time to 254 nm irradiation.

Two variants of GFP were compared to GFP for photochromic behavior. The GFP was mutated by changing Thr203 to Ser (T203S) and Ser205 to Thr (S205T) while leaving Ser65 unchanged. Referring to FIG. 3, the excitation spectra of purified GFP with the mutations T203S are shand S205T are shown as a function of exposure to 254 nm irradiation under the same conditions as in FIG. 2. The mutation S205T alone resulted in no change in photochromic behavior in comparison to WT. The excitation peak attributable to the state created by UV irradiation has been shifted from 480 nm to 490 nm relative to WT GFP. The enhancement of the excitation at 490 nm is a factor of 11.8 after irradiation. Although 254 nm was used to generate the graphs shown in FIGS. 2 and 3, wavelengths as long as 365 nm can be used to convert states. Mutations can improve the photochromic conversions both to shorter and longer excitation wavelengths than the native states.

Two other variants of GFP, S65G/S72A/T203F ("T203F" herein) and S65G/S72A/T203Y ("T203Y" herein), were prepared that exhibited photochromic behavior. T203F and T203Y differ only by the presence and absence, respectively, of a hydroxyl group in proximity of the chromophore in the GFP. Bulk absorption and emission spectra of T203F and T203Y are shown in FIGS. 4A–4D. The absorption of T203F (FIG. 4A, solid line emission) shows a small hump near 405 nm in addition to the dominant peak at 510 nm. Excitation at 488 nm produces the emission spectrum (FIG. 4A, dotted line emission) while excitation at 400 nm gives an emission maximum at 455 nm, rather than the usual 525 nm, shown in FIG. 1B. The long-wavelength absorption and emission probably correspond to the anionic state $A^{31}$, and the short-wavelength absorption likely arises from a small fraction of molecules with neutral chromophores (state N). See, for example, Cubitt, A. B., et al. *Trends in Biochem. Sci.* 20:448 (1995); and Dickson, R. M., et al. *Science* 274:966–969 (1996). The absorption spectrum of T203Y, shown in FIG. 4C has a smaller maximum at 400 nm, but 488 nm pumping yields an emission peaking at 525 nm that appears almost identical to the emission from T203F. In contrast, excitation of T203Y at 400 nm yields weak emission at 470 nm and a strong emission at 525 nm.

The photochromic fluorescent protein moieties can be used, for example, in applications involving fluorescence resonance energy transfer (FRET). Such applications can detect events as a function of the movement of fluorescent donors and acceptor towards or away from each other. One or both of the donor/acceptor pair can be a fluorescent protein. The efficiency of FRET depends on the separation distance and the orientation of the donor and acceptor fluorescent protein moieties. See, for example, Forster, T. *Ann. Physik* 2:55–75 (1948); and Energy transfer parameters of aromatic compounds, Academic Press, New York and London (1973). FRET is a nondestructive spectroscopic method that can monitor proximity and relative angular orientation of fluorophores in living cells. See, for example, Adams, S. R., et al., *Nature* 349:694–697 (1991), and Gonzalez, J. & Tsien, R. Y. *Biophy.J.* 69:1272–1280 (1995).

The photochromic fluorescent protein moieties can be immobilized in a host matrix, such as a polyacrylamide (PAA) gel. Other possible hosts for the photochromic fluorescent protein moieties include agarose gels, hydrogen-bonded polymers such as poly(vinyl alcohol), poly (electrolytes), viscous liquids, cell cytoplasm. The PAA gel host provides pore sizes small enough for convenient immobilization of individual protein molecules. See, for example, Fawcett, J. S. & Morris, *C.J.O.R. Sep. Sci.* 1:9 (1966).

Immobilized photochromic fluorescent protein moieties can be imaged as single molecules. See, for example, Dickson, R. M. et al. *Science* 274:966–969 (1996); and Moerner, W. E. *Science* , 265:46–53 (1994). Photochromic GFPs can be used in biological applications such as marking cell structures with a focused beams and monitoring their subsequent diffusion or trafficking. For a description of marking cell structures with GFP, see, Yokoe, H. & Meyer, T. *Nature Biotechnology* 14:1252 (1996).

Photochromic molecules can be used as potential recording media for optical storage of information. See, for example, Irie, M. & Mori, M. *J. Org. Chem.* 53:803 (1988); Parthenopoulos, D. A. & Rentzepis, P. M. *Science* 245:843 (1989); Hanazawa, M., et al. *J. Chem. Soc. Chem. Commun.* 206 (1992); Dvornikov, A. S., et al. *J. Phys. Chem.* 98:6746–6752 (1994); Dvornikov, A. S. & Rentzepis, P. M. *Opt. Mem. Neur. Netw.* 3:75–86 (1994); U.S. Pat. No. 4,471,470; and U.S. Pat. No. 5,325,324. The photochromic fluorescent protein moieties can be used in single-molecule optical storage with GFP, and multi-molecule optical storage with GFP. The photochromic fluorescent protein moieties can be immobilized on a surface or on a matrix, such as PAA gel. Single-molecule optical storage can be achieved. See, W. E. Moerner, *Science* 265:46 (1994), in reference to low temperature devices. The device can function at room temperature because of the stability of the states of the photochromic fluorescent protein moieties.

Information can be stored by switching between states of the photochromic fluorescent protein moiety by irradiation. Reading can be achieved, for example, by irradiating with low intensities. Similarly, writing and erasing can be achieved, for example, by irradiating with high intensities. Periodically, it can be necessary to refresh a state by reading the state of the photochromic fluorescent protein moiety and rewriting with high intensity irradiation.

Different optical storage schemes can be implemented using the photochromic fluorescent protein moieties. First, two-dimensional, bit-oriented read/write/erase optical storage can be used. In this scheme, individual bits are addressed on a planar surface, i.e., by rotating a disk under a focusing lens which produces a diffraction-limited spot of light on the disk. Each bit is written by a different diffraction-limited spot on the disk. The diffraction-limited spot has a diameter on the order of the optical wavelength used for writing. With a photochromic fluorescent protein moiety (i.e., GFP), a recording layer can be made either by spin coating monomers on the surface of the disk before gelation or attaching the photochromic fluorescent protein moiety to a surface via a covalent bond (i.e., as a self-assembled monolayer). Alternatively, a recording layer can be fabricated by sandwiching a PAA gel containing the photochromic fluorescent protein moiety in between two transparent glass layers. Using T203F or T203Y, for example, the read/write operation can proceed using 488 nm to write (and read), 405 nm to erase, or vice-versa.

A second approach to optical storage is near-field optical storage. In this scheme, an optical device, like a pulled fiber tip or a solid immersion lens, is used to make a laser spot much smaller diffraction-limited spot (i.e., smaller than the optical wavelength). See, for example, Betzig, E. & Trautman, J. *Science* 257:189 (1992); and Terris, B. D., et al. *Appl. Phys. Lett.* 68:141 (1996). For example, a near-field fiber tip can generate an irradiation region that is about 50 nm in diameter. The solid immersion lens is more robust, but it produces a spot approximately 300 nm in diameter. In either case, much higher areal densities can be achieved than with diffraction-limited spots. For this type of storage, the recording layer must be very close to either the tip or the immersion lens. The photochromic fluorescent protein moiety (e.g., GFP) can be reactively attached to a fused silica or glass surface that has been silanized and made functional for attachment to free amines of, for example, lysine, or to sulfhydryl functionality of cysteine amino acids. By patterning of the surface functionalization, single GFP molecules can be distributed in an array on the surface. Using T203F or T203Y, for example, the read/write operation can proceed with 488 nm to write (and read), 405 nm to erase, or viceversa. It is not necessary for the read, write, and erase wavelengths to be focused tightly.

A third approach to optical storage is holographic optical storage. In this scheme, higher storage densities can be achieved by using an optically thick hologram for the recording. The actual recording is made my locally changing the refractive index or the optical absorption in the material. Read/write volume holographic storage based on photorefractive materials is generally described in Sincerbox, G.T. *Optical Materials* 4:370 (1995). A recent demonstration using $LiNbO_3$ is described in Heanue, J. F. et al. *Science* 265:749 (1994). A review of holographic memory using general materials, including (write-once) photopolymers is given in D. Psaltis and F. Mok, *Scientific American* November 1995, p. 70. In holographic storage, an image-bearing beam and a reference beam are both impressed upon the material, and the change in the optical properties ensues at the locations in the material bearing high intensities of irradiation to record an image. After recording, when only the reference beam is turned on, a diffracted beam appears which is a copy of the original image beam. To erase the stored image, a uniform beam is left on for a longer period of time. To achieve high information density, many holograms can be written in the same volume by using a different angle, phase, or frequency of reference beam for each image. Holographic optical storage can provide high data transfer rates by parallel readout, and high density of storage.

A photochromic fluorescent protein moiety (i.e., GFP) can be fabricated in a thick gel material, and two laser beams at 488 nm can be used to write a hologram in the gel. The hologram can be read with illumination at 488 nm by fluorescence or by diffraction. The hologram can be erased by 405 nm irradiation or by uniform exposure to 488 nm. Alternatively, the material can be irradiated uniformly with 488 nm to drive all the molecules into the N state. Subsequent irradiation with two beams at 405 nm can produce a hologram in the gel. Erasure in this case can require exposure to 488 nm or uniform 405 nm.

A fourth approach to optical storage is two-photon volumetric optical storage. Photochromic materials for two-photon three dimensional optical storage have been reviewed by Dvornikov, A. S., et al. *J. Phys. Chem.* 98:6746 (1994), and by Dvornikov, A. S. & Rentzepis, P. M. *Opt. Mem. Neur. Netw.* 3:75 (1994). See also, for example, U.S. Pat. No. 5,325,324. In this scheme, localization of a written bit in a three dimensional medium can be achieved by using a nonlinear interaction with the material, such as a two-photon optical excitation. A laser beam of long wavelength and high intensity can be used to pump a two-photon transition, which causes a change in the optical properties of the material. The intensity dependence is I-squared or higher. The two-photon approach results in a high degree of localization of the altered region in all three dimensions. Next, a second two-photon process can be used for readout (e.g., by fluorescence). Erasing of the medium can be done by one-photon irradiation of the medium at another wavelength. One advantage of a two-photon mechanism is that essentially erasing does not occur during reading.

By using a photochromic fluorescent protein moiety in two-photon volumetric optical storage such as, for example, T203F or T203Y, the writing step can be caused by illuminating the moiety with two photons of 2×488 nm wavelength. The reverse (i.e., erasing) step can be produced by 2×405 nm irradiation. If less spatial localization is required (e.g., in the erasing step), native one-photon irradiation can be used. A cube of water-filled gel (i.e., a PAA gel) containing a photochromic fluorescent protein moiety (i.e., a GFP) can be used in a volumetric optical storage system.

Screening methods can be used to identify photochromic fluorescent protein moieties having an increased or particular photochromic response. The bacteria are transformed with GFP cDNA (containing a large number of different mutations) and spread onto agar plates following standard molecular biological methods such as described in chapter 1 of *Molecular Cloning, a Laboratory Manual,* 2nd ed., by Sambrook, J., Fritsch, E. F. & Maniatis, T., Cold Spring Harbor Laboratory Press (1989). The plate is then illuminated with two different wavelengths A and B in succession. Two separate images can be captured (I(A1) and I(B1)) with an electronic camera and computer system. The plate is then illuminated with a high dose of light at a third wavelength C, which can be the same as A or B, or different from both. The third wavelength may photoisomerize any appropriately photochromic GFPs, resulting in a change in the fluorescence response of the plate. After the exposure, the plate is illuminated with the two original wavelengths A and B and two more images I(A2) and I(B2) are captured. The ratio images I(A2)/I(A1), I(B2)/I(B1), as well as the ratio of these two ratios, I(A2)I(B1)/I(A1)I(B2) can be calculated and displayed. Colonies can be identified that deviate significantly from the mean behavior by examination of the ratio images for any of these three ratios. The experimenter can pick up colonies of interest. Alternatively, the computer can robotically pick up colonies of interest using feature detection and mechanical manipulation capabilities.

All of the mutants discussed herein show up in all three ratio images: I(A2)/I(A1); I(B2)/I(B1); and I(A2)I(B1)/I(A1)I(B2). The reason for showing all three is that there might be mutants which get brighter or dimmer at all wavelengths, so that I(A2)/I(A1) and I(B2)/I(B1) might be equal to each other, though different from 1. Since the ratio of ratios would be 1, these mutants would be missed if one did not check the constituent ratios as well.

The method can be extended by skipping image capture step to obtain I(A1) and I(B1). First, the plate is exposed to wavelength C, and fluorescent images I(A2) and I(B2) are captured. Next, the plate is exposed to wavelength D, and fluorescent images I(A3) and I(B3) are captures. Colonies can be chosen on the basis of ratio images I(A3)/I(A2), I(B3)/I(B2), and I(A3)I(B2)/I(A2)I(B3). This method can be used, for example, to find mutants based on T203F or T203Y that optimize the conversion from the short wavelength state N back to the normal long wavelength $A^{31}$ state. The first irradiation wavelength C can be 488 or 514 nm in order to build up the population in the N state, then wavelength D can be 405 nm to test the back conversion.

Preferably, in the above procedures, an exact replica of the colonies on a plate is made. This can be done by pressing a nitrocellulose filter onto the agar plate so that some but not all the bacteria that make up each colony stick to the nitrocellulose. The nitrocellulose replica carries a spatially precise mirror-image replica of the colonies on the original agar plate. All the light exposures and imaging are performed on the replica on nitrocellulose because nitrocellulose has a lower background fluorescence than agar. However, the actual bacteria to be propagated are picked off the corresponding colonies in the agar original, which has not been subjected to the potentially harsh treatments that might jeopardize the survival and subsequent multiplication of the bacteria. The computer system can reverse the mirror-image views of the replica colonies to ease registration of those images with the original agar plate.

It is possible to perform similar screenings with chemical treatments rather than light exposures. For example, the chemical treatments can include changing the pH, changing calcium ion concentration, adding cyclic GMP, adding a protein kinase, or adding a protease. The bacteria can be lysed so that added reagents can access the GFPs. The chemical approach may make replica plating more necessary.

The Examples described below are illustrative of the disclosed method; however, many alternatives, modifications and variations will be clear to those skilled in the art.

EXAMPLES

Preparation of Mutants

GFP was expressed in *E. coli* using the expression plasmid PRSET (Invitrogen), in which the region encoding GFP was fused in frame with nucleotides encoding an N-terminal polyhistidine tag. Sequence changes were introduced by site directed mutagenesis using the Bio-Rad mutagenesis kit. See, Kunkel, T. A., et al. Meth. Enzymol. 154:367–382 (1987). The sequence changes were confirmed by sequencing. The recombinant proteins were expressed in the bacterial strain BL21(DE3) after induction with IPTG (0.5 nM) at room temperature and purified by Ni affinity chromatography.

Single molecule imaging

Single molecules of the red-shifted (relative to WT) GFP mutant 10C (S65G/V68L/S72A/T203Y), T203F, and T203Y were individually immobilized in PAA gels and were imaged. The samples were prepared by the methods described in Dickson, R. M., et al. Science 274:966–969 (1996) from $10^{-10}$M solutions of protein diluted in 1 mg/ml BSA. PAA gels (T=15%, C=5% without SDS) were prepared in pH 7 phosphate buffered saline doped with the protein. Excitation with a 488 nm laser (2000 W/cm$^2$) occurred in the total internal reflection geometry, and the emission was imaged with 250 nm resolution with a Nikon inverted microscope with an Omega 535DF55 filter and a Princeton Instruments slow-scan liquid nitrogen cooled CCD detector (Exposure time: 100 ms; pixel size: 120 nm×120 nm at the focal plane). For the imaging of the T203F and T203Y PAA gels, a Princeton Instruments Gen IV intensified CCD was utilized for detection. Intensity versus time traces were generated by summing the pixels for each molecule from sequential 100 ms images for a total of 90 seconds. 405 nm irradiation was produced by a Hg arc lamp with line filter through the epi-illumination port (1 W/cm$^2$).

The 10C mutant has one absorption maximum at 513 nm and a strong emission at 527 nm. The PAA gel host provided pore sizes small enough for convenient and relatively complete immobilization of each protein molecule, while maintaining the naturally fluorescent, native conformation. See, Dickson, R. M. et al. *Science* 274:966–969 (1996); and Fawcett, J. S. & Morris, *C.J.O.R. Sep. Sci.* 1:9 (1966). Several seconds (e.g., up to tens of seconds) of fluorescence emission from 10C were observed.

The fluorescence emission was followed by several seconds with no emission. After further time elapses, fluorescence emission resumes. This "on/off" behavior (i.e., blinking) repeats over the course of many minutes. The on/off behavior and the strong polarization of the excitation can support the single molecule character of the emission. Detected count rates of 5000–6000 photons per second at 2000 W/cm$^2$ pumping intensity (i.e., about 150,000 excitations per second) can be achieved.

Using a single-molecule imaging apparatus described above and in Dickson, R. M. et al. *Science* 274:966–969 (1996), and Moerner, W. E. *Science*, 265:46–53 (1994). Images of the emission (excitation at 488 nm) from the PAA gel containing GFP mutants showed clear, separated single-molecule peaks, as shown in FIGS. 5A–5D. Three T203Y molecules are shown as A, B, and C. A and B are brighter due to closer proximity to the gel-coverslip interface and more favorable dipole/laser polarization alignment than molecule C. FIG. 5D is a graph depicting a line intensity profile at the position of the arrow.

Figure 5E:
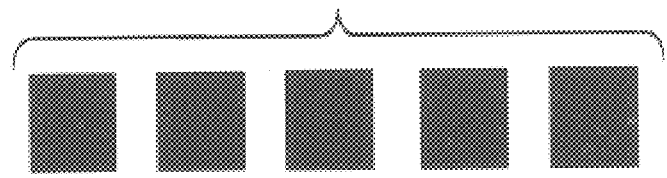
FIG. 5E is a series of images of fluorescence emission from a single T203F GFP molecules after 90 seconds of 488 nm irradiation followed by 5 minutes in the dark.

Generally, each GFP molecule remains in a nonfluorescent state after the emission of an average of about $10^6$ photons. The final nonemissive state was long-lived. After 5 minutes in the dark (i.e., no pumping), the single molecules of T203F were consistently nonemissive upon re-irradiation at 488 nm (FIG. 5E).

Figure 5F:
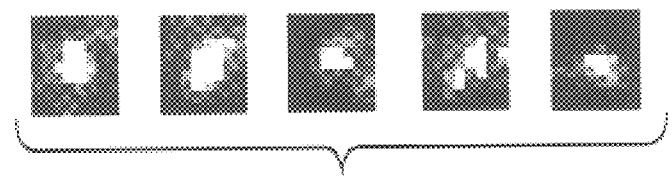
FIG. 5F is a series of images of fluorescence emission from a single T203F GFP molecules after 90 seconds of 488 nm irradiation followed by 5 min irradiation at 406 nm.

The emissive state was reproducibly recovered by irradiating the GFP mutant at 405 nm for 5 minutes prior to excitation with 488 nm radiation, as shown in FIG. 5F. FIG. 5F is a series of images of fluorescence emission from a single T203F GFP molecules after 90 seconds of 488 nm irradiation followed by 5 min irradiation at 406 nm. The first frame shows the same single molecules as in FIG. 5E in the bright state. Similar switching behavior occurred for T203Y. This represents optically-driven switching behavior in a single molecule of GFP at room temperature. The behavior is similar to two-state switching in low temperature systems. See, for example, Moerner, W. E., et al. *J. Phys. Chem.* 98:7382 (1994).

Referring to FIGS. 6A and 6B, the on/off behavior of the PAA gels containing GFP mutants T203Y and T203F was observed in the fluorescence intensity versus time of each of the triple mutants. Excitation intensity was 2000 W/cm$^2$. Only the first 16 seconds of data are shown in FIGS. 6A and 6B. There was no oxygen-exposure dependence of the on/off behavior of the GFP gels. Oxygen was not removed from samples on which data are presented. As a control, separate samples were deoxygenated by several minutes of bubbling with He gas and studied. No differences between oxygenated and deoxygenated samples were observed. During several minutes of illumination at 488 nm, each molecule exhibited several bright periods.

Plots of intensity versus time, similar to FIGS. 6A and 6B, for numerous single molecules were analyzed to develop histograms of on/off times in a fashion similar to that used in single ion channel recordings. See, Sakmann, B. & Neher, E. (Plenum Press, New York, 1995). The intervals for the single molecules were combined, and only the high intensity data (2000 W/cm$^2$) yielded a high signal-to-noise ratio to reliably distinguish bright and dark by a single threshold intensity of light.

Autocorrelation analysis

The autocorrelation function, $C(\tau)$, can be defined for discrete data points, $$C(\tau) = \sum_{t=0}^{N} (I(t) - \bar{I})(I(t+\tau) - \bar{I}) \Big/ \sum_{t=0}^{N} (I(t) - \bar{I})^2,$$

where $\bar{I}$ is the average intensity, t is the time summed from 0 to N 100 ms intervals, and I(t) is the time dependent fluorescence intensity. Confidence limits were generated on the autocorrelations such that any values within the limits were consistent with zero. See, for example, Box, G.E.P. & Jenkins, G. M. "Time Series Analysis Forecasting and Control," Holden-Day, Inc., San Francisco, (1970).

Autocorrelation (AC) analysis was used obtain more information from time traces at lower power levels. AC has been successfully applied to monitor single-molecule dynamics in many other situations. See, "Single Molecule Optical Detection, Imaging, and Spectroscopy," Basché, T., Moerner, W. E., Orrit, M. & Wild, U.P., Editors, Verlag-Chemie, Munich, 1997. The statistically significant portions of the decay curves beyond the short time correlation spike arising from band-limited noise were fit to an exponential decay. T203Y and T203F single molecule autocorrelations and confidence limits are presented with the fluorescence trajectories are presented in FIGS. 6C and 6D. Referring to FIGS. 6C and 6D, the "on" time histograms were easily fit by a single exponential decay. The time constant for T203Y was 0.86 seconds (N=89) and the time constant for T203F was 0.71 seconds (N=97). The "off" time histograms could be fit to a biexponential decays for both mutants with a short decay time of about 1 second and a long decay time of tens of seconds. The determination of the long component was limited by the data collection time of 90 seconds.

Figure 7A:
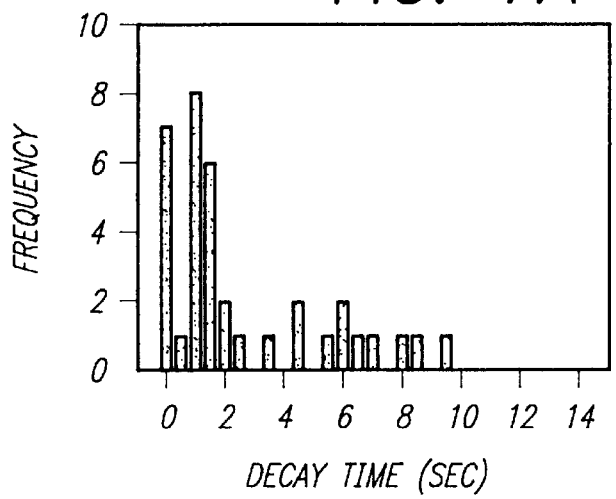
FIGS. 7A–7F are graphs depicting histograms of single molecule autocorrelation times $\tau_c$ as a function of incident intensity.
Figure 7B:
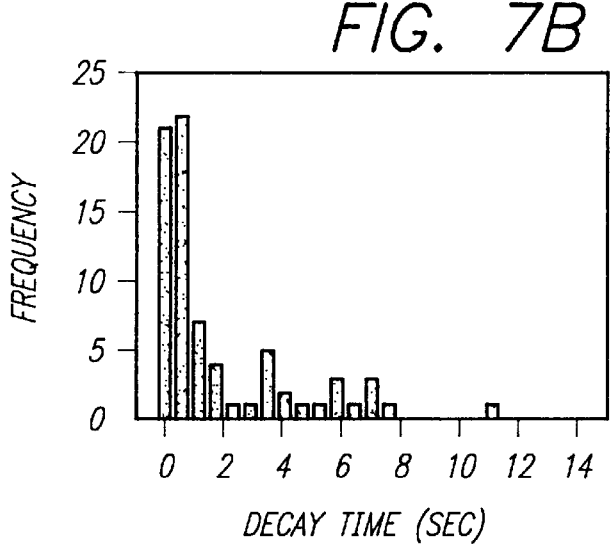
Figure 7C:
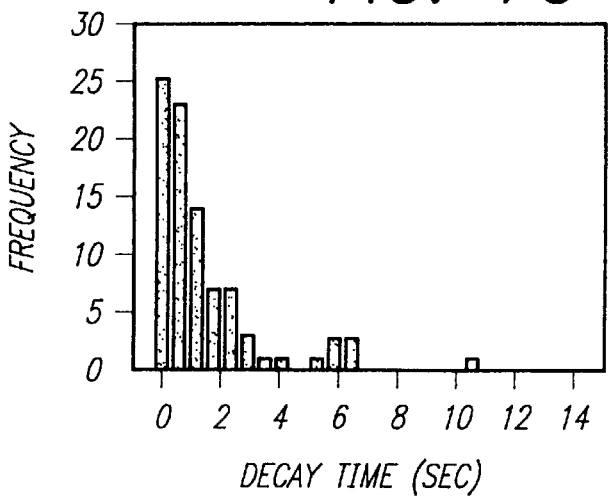
Figure 7D:
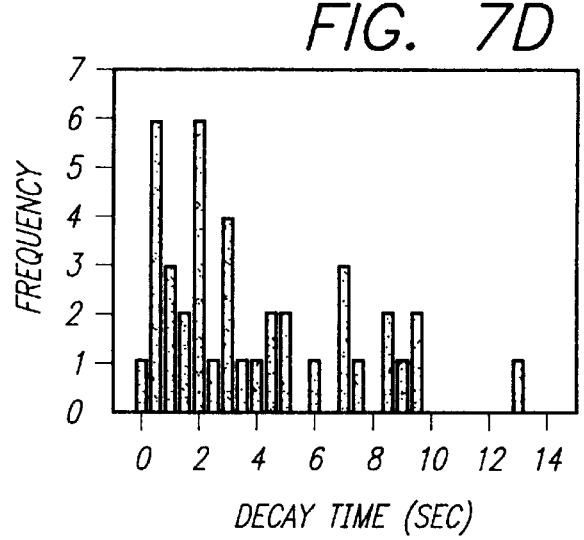
Figure 7E:
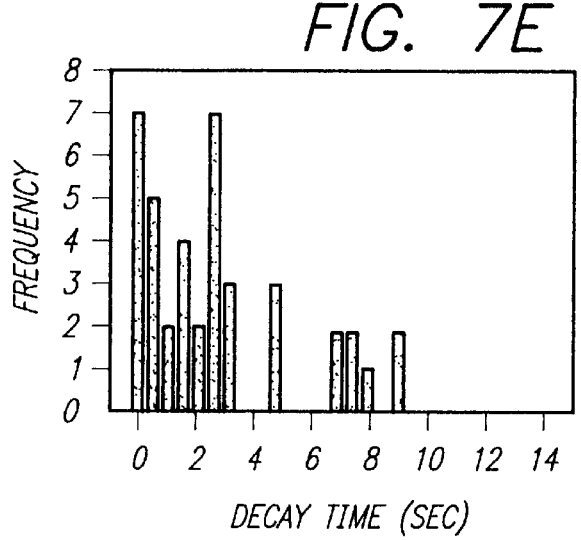
Figure 7F:
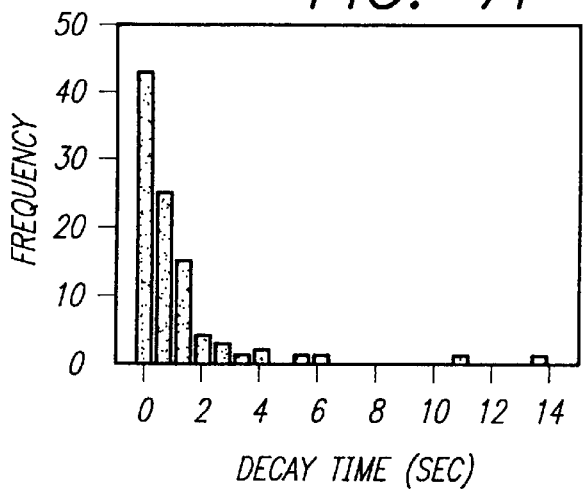

The autocorrelation time, $\tau_c$, reflects the average period of the on/off behavior. Histograms of the $\tau_c$ values from 377 individual GFP molecules are presented in FIGS. 7A–7F. The average single molecule autocorrelation times at three different power levels are given in Table II were determined from the histograms in FIGS. 7A–7F. FIGS. 7A, 7B, and 7C correspond to T203Y at 100 W/cm$^2$, 500 W/cm$^2$, and 2000 W/cm$^2$, respectively. FIGS. 7D, 7E, and 7F were generated from T203F data at 100 W/cm$^2$, 500 W/cm$^2$, and 2000 W/cm$^2$, respectively. The quoted errors correspond to 80% confidence limits.

TABLE II

| Laser Intensity* | GFP Mutant | |
|---|---|---|
|  | S65G/S72A/T203Y | S65G/S72A/T203F |
| 100 W/cm$^2$ | 2.82 ± 0.62 (N = 36) | 4.78 ± 0.80 (N = 41) |
| 500 W/cm$^2$ | 2.01 ± 0.36 (N = 74) | 2.91 ± 0.57 (N = 40) |
| 2000 W/cm$^2$ | 1.61 ± 0.27 (N = 89) | 1.37 ± 0.27 (N = 97) |

*Intensity was measured at the gel/coverslip interface.

The autocorrelation time depends on the irradiation power; $\tau_c$ decreases by a factor of 2 when the incident intensity is increased 20-fold. Saturation of the transition is unlikely, based on estimates of the saturation intensity determined from the measured extinction coefficients of the GFPs, and by the observed linearity of the emission rate with pumping intensity. Referring to FIGS. 7A–7F, the T203F histograms show a stronger power dependence than does T203Y, i.e., shorter $\tau_c$ with increasing intensity. Since the autocorrelation measures how the fluorescence intensity correlates with itself in time, faster and less power dependent autocorrelation decays of T203Y relative to those of T203F indicate that T203Y exhibits a lower energy pathway to fluorophore activation and inactivation.

Without intending to be bound, the dynamics of the two GFP mutants suggest the model shown in FIG. 1. The diagram is consistent with the experimental observations as described in the text. Dotted lines are suggested pathways, while solid lines are pathways directly supported by the data. For simplicity, the states are depicted to be connected as A$^-$<->I<->N, but they may be connect as I<->A$^-$<->N. Since T203Y and T203F have strong absorption maxima near 513 nm, we define the bright state as the anionic form of the chromophore which absorbs 488 nm excitation and emits photons at 535 nm, and the dark states as those which do not. The on/off emission on the time scale of many seconds indicates that the there is a dark state, I, from which spontaneous return to A$^-$ occurs. Processes $P_1$ populate the state I, although the very weak power dependencies observed in the $\tau_c$ values of both mutants suggest that the A$^-$<->I transition occurs predominantly in the ground state. In addition, there can be another dark state which is eventually reached with lower probability (state N, process $P_2$) and has a long lifetime (>5 minutes) in the absence of 488 nm. N appears to be the neutral form of the GFP mutant. The ground state barrier for N->I is apparently large enough for N to be stable at room temperature. The presence of this additional dark state is consistent with the biexponential dark time distribution. Excitation at 405 nm, however, does regenerate state A$^-$, by some third process $P_3$, showing that light-induced conversion from the neutral to the anionic state occurs when higher energy photons are present.

Figure 4A:
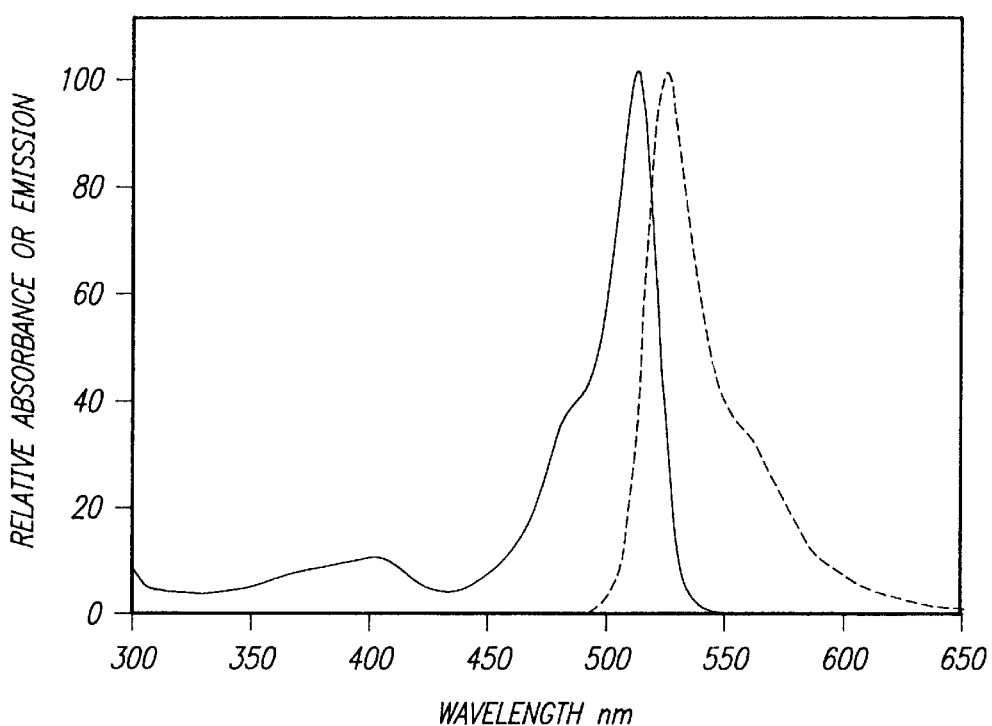
FIG. 4A is a graph depicting the bulk spectra of the GFP mutants T203F excited by 488 nm (solid line, absorption; dotted line, emission).
Figure 4B:
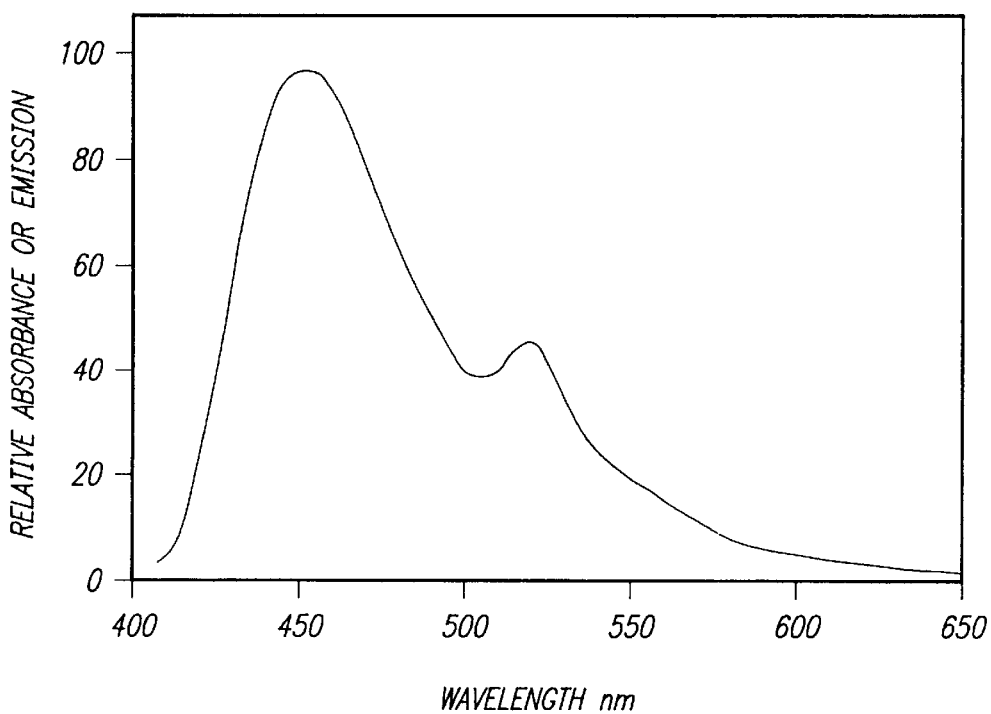
FIG. 4B is a graph depicting the bulk spectra of the GFP mutant T203F emission excited by 400 nm.
Figure 4C:
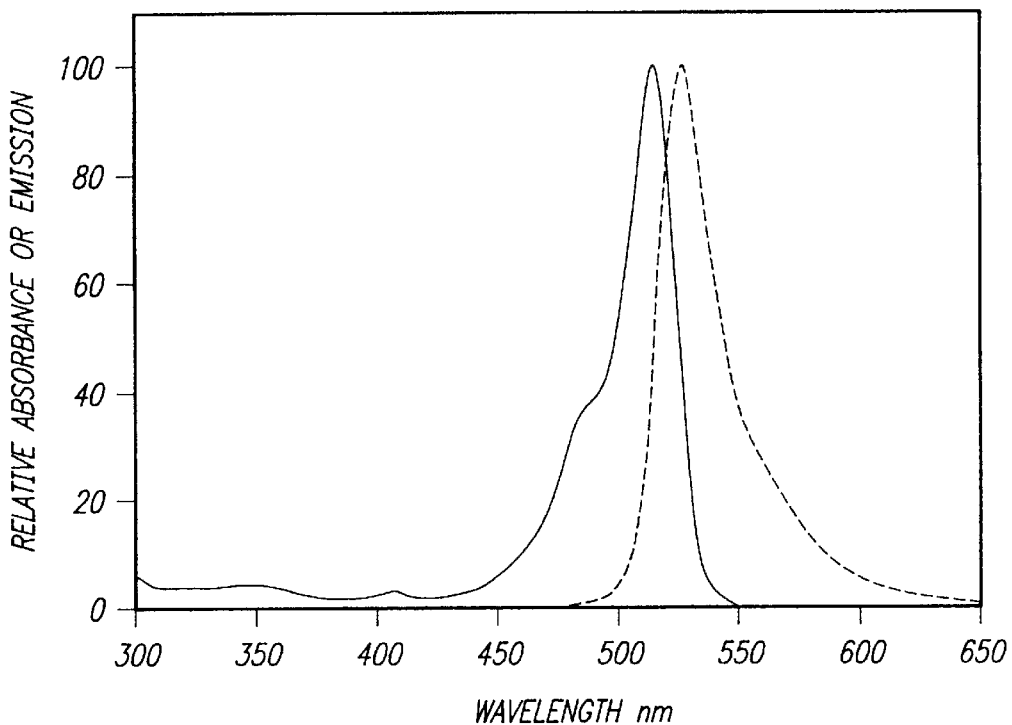
FIG. 4C is a graph depicting the bulk spectra of the GFP mutant T203Y emission excited by 488 nm (solid line, absorption; dotted line).
Figure 4D:
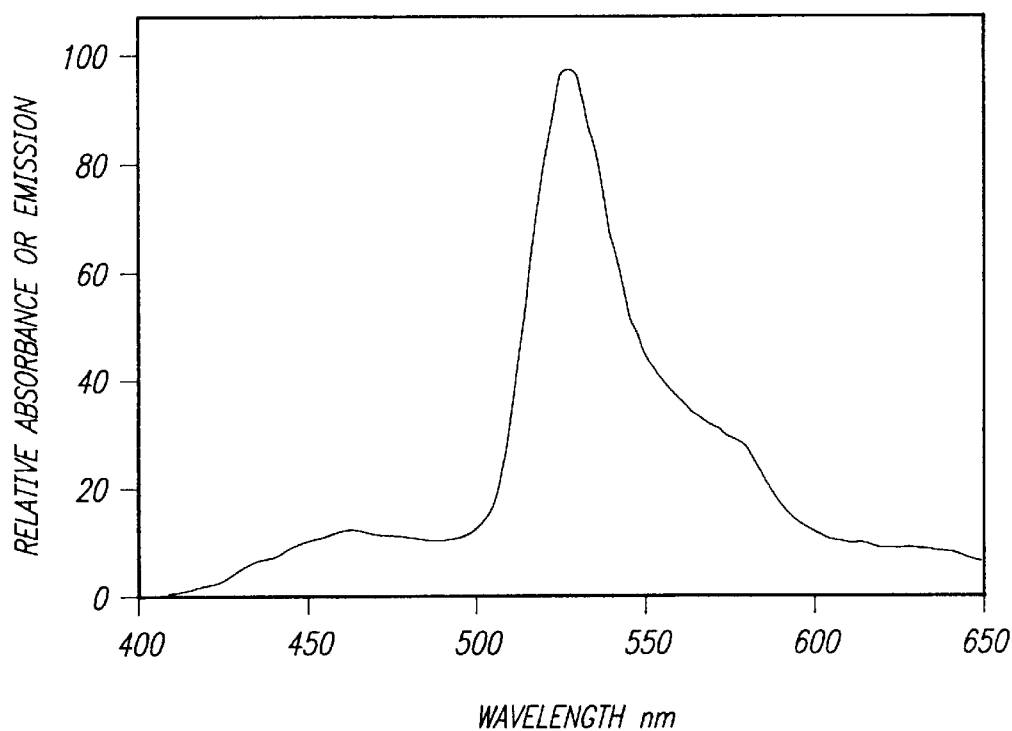
FIG. 4D is a graph depicting the bulk spectra of the GFP mutant T203Y emission excited by 400 nm.

The data presented above in combination with the recent crystal structure determinations of GFP (see, for example, Ormo, M., et al. *Science* 273:1392 (1996); Yang, F., et al. *Nature Biotech.* 14:1246 (1996); and Brejc, K., et al. *Proc. Nat. Acad. Sci., USA* 94:2306–2311 (1997)) provide the unique opportunity to study how the structure of the chromophore's salvation shell affects its photophysical properties. The autocorrelation analysis helps describe the ground state, while the bulk spectra in FIGS. 4A–4D and the single molecule switching behavior observed under 405 nm excitation helps describe the excited state interactions. The single WT emission band indicates that neutral/anionic interconversion occurs upon excitation via a common excited state. See, Chattoraj, M., et al. *Proc. Nat. Acad. Sci., USA* 93:8362 (1996). In contrast, the chromophore in T203F, excited by irradiation at 400 nm, mainly emits near 460 nm, rather than 525 nm (FIG. 4B). This suggests a higher barrier for excited state deprotonation than in WT. T203Y excited by irradiation at 400 nm emits predominantly, but not completely, near 525 nm (FIG. 4D). This may either reflect deprotonation of the excited state facilitated by the tyrosine hydroxyl or direct excitation of the greater excess of pre-formed anionic chromophores.

From the above description, the essential characteristics of the present invention can be ascertained. Without departing from the spirit and scope thereof, various changes and modifications of the invention can be made to adapt it to various usages and conditions. Thus, other embodiments are also within the claims.

What is claimed is:

1. An optical memory device, comprising:
   a photochromic fluorescent protein moiety that is capable of being converted from a first fluorescent state to a second fluorescent state by irradiation with a writing wavelength in an optical memory device,
   wherein said first fluorescent state has a first excitation wavelength maximum, and
   wherein said photochromic fluorescent protein moiety is capable of being converted from said second fluorescent state to said first fluorescent state by irradiation with an erasing wavelength in an optical memory device.

2. The optical memory device of claim 1, wherein said first fluorescent state and said second fluorescent state are substantially stable at room temperature.

3. The optical memory device of claim 1, wherein said photochromic fluorescent protein moiety is an Aequorea-related photochromic fluorescent protein moiety.

4. The optical memory device of claim 1, wherein said second fluorescent state has a second excitation wavelength maximum, said second excitation wavelength maximum being longer than said first excitation wavelength maximum.

5. The optical memory device of claim 3, wherein excitation of said second fluorescent state at said second excitation maximum produces an intensity that is at least four times greater than said intensity of said first fluorescent state at said second excitation wavelength maximum.

6. The optical memory device of claim 4, wherein excitation of said second fluorescent state at said second excitation wavelength maximum produces an intensity that is at least eight times greater than said intensity of said first fluorescent state at said second excitation wavelength maximum.

7. The optical memory device of claim 3, wherein said second fluorescent state has a second excitation wavelength maximum, said second excitation wavelength maximum being shorter than said first excitation wavelength maximum.

8. The optical memory device of claim 3, wherein said photochromic fluorescent protein moiety includes an amino acid substitution of T203.

9. The optical memory device of claim 3, wherein said photochromic fluorescent protein moiety includes an amino acid substitution T203F, T203Y, or T203S.

10. The optical memory device of claim 3, wherein said photochromic fluorescent protein moiety includes amino acid substitutions S65G/S72A/T203F, S65G/S72A/T203Y, or T203S/S205T.

11. The optical memory device of claim 3, wherein said photochromic fluorescent protein moiety is a single polypeptide.

12. The optical memory device of claim 3, further comprising a medium including a plurality of said photochromic fluorescent protein moieties distributed throughout a medium.

13. The optical memory device of claim 12, wherein said medium is configured as a planar surface or a volume.

14. The optical memory device of claim 13, wherein said medium further includes polyacrylamide.

15. The optical memory device of claim 12, wherein each of said photochromic fluorescent protein moieties is individually addressable in said medium.

16. An optical memory device comprising:
   an Aequorea-related photochromic fluorescent protein moiety which is capable of being converted from a first fluorescent state to a second fluorescent state by irradiation with a writing wavelength in an optical memory device,
   wherein said photochromic fluorescent protein moiety is capable of being converted from said second fluorescent state to said first fluorescent state by irradiation with an erasing wavelength in an optical memory device, and
   wherein a medium including a plurality of said photochromic fluorescent protein moieties distributed throughout said medium, said medium being configured as a planar surface or a volume,
   further wherein said first fluorescent state has a first emission wavelength maximum, said first fluorescent state is capable of being excited by a reading wavelength in an optical memory device.

17. The optical memory device of claim 16, wherein said first fluorescent state and said second fluorescent state are substantially stable at room temperature.

18. The optical memory device of claim 16, wherein said second fluorescent state has a second excitation wavelength maximum, said second excitation wavelength maximum being longer than said first excitation wavelength maximum.

19. The optical memory device of claim 16, wherein excitation of said second fluorescent state at a second excitation wavelength maximum produces an intensity that is at least four times greater than said intensity of said first fluorescent state at said second excitation wavelength maximum.

20. The optical memory device of claim 16, wherein said second fluorescent state has a second excitation wavelength maximum, said second excitation wavelength maximum being shorter than said first excitation wavelength maximum.

21. The optical memory device of claim 16, wherein said photochromic fluorescent protein moiety includes an amino acid substitution of T203.

22. The optical memory device of claim 16, wherein said photochromic fluorescent protein moiety includes an amino acid substitution T203F, T203Y, or T203S.

23. The optical memory device of claim 16, wherein said photochromic fluorescent protein moiety includes amino acid substitutions S65G/S72A/T203F, S65G/S72A/T203Y, or T203S/S205T.

24. The optical memory device of claim 16, wherein said medium further includes polyacrylamide.

25. The optical memory device of claim 16, further comprising a medium including a plurality of said photochromic fluorescent protein moieties distributed throughout said medium.

26. The optical memory device of claim 24, wherein each of said photochromic fluorescent protein moieties is individually addressable in said optical memory device.

27. A composition of matter, comprising:
   a photochromic fluorescent protein moiety capable of being converted from a first fluorescent state to a second fluorescent state by irradiation with a writing wavelength in an optical memory device,
   wherein said first fluorescent state has a first excitation wavelength maximum, said second fluorescent state has a second excitation wavelength maximum, excitation of said second fluorescent state at said second wavelength excitation maximum produces an intensity that is at least four times greater than said intensity of said first fluorescent state at said second excitation wavelength maximum.

28. The composition of matter of claim 27, wherein said first fluorescent state and said second fluorescent state are substantially stable at room temperature.

29. The composition of matter of claim 27, wherein said photochromic fluorescent protein moiety is an Aequorea-related photochromic fluorescent protein moiety.

30. The composition of matter of claim 27, wherein said photochromic fluorescent protein moiety includes an amino acid substitution of T203.

31. The composition of matter of claim 27, wherein said photochromic fluorescent protein moiety includes an amino acid substitution T203F, T203Y, or T203S.

32. The composition of matter of claim 27, wherein said photochromic fluorescent protein moiety includes amino acid substitutions S65G/S72A/T203F, S65G/S72A/T203Y, or T203S/S205T.

33. The composition of matter of claim 27, wherein said photochromic fluorescent protein moiety is a single polypeptide.

34. The composition of matter of claim 27, wherein said photochromic fluorescent protein moiety is capable of being converted from said second fluorescent state to said first fluorescent state by irradiation with an erasing wavelength in an optical memory device.

35. The composition of matter of claim 27, wherein said second excitation wavelength maximum is longer than said first excitation wavelength maximum.

36. The composition of matter of claim 27, wherein said second fluorescent state has a second emission wavelength maximum and said first fluorescent state has a first emission wavelength maximum,
wherein said second emission wavelength maximum is shorter than said first emission wavelength maximum.

37. The composition of matter of claim 27, wherein excitation of said second fluorescent state at said second excitation wavelength maximum produces an intensity that is at least 8 times greater than said intensity of said first fluorescent state at said second excitation wavelength maximum.

38. A method for storing and recovering information comprising:
addressing a photochromic fluorescent protein moiety which is capable of being converted from a first fluorescent state to a second fluorescent state by irradiation with a writing wavelength in an optical memory device, wherein said first fluorescent state has a first excitation wavelength maximum, and
wherein said photochromic fluorescent protein moiety is capable of being converted from said second fluorescent state to said first fluorescent state by irradiation with an erasing wavelength in an optical memory device, in a medium including a plurality of said photochromic fluorescent protein moieties;
exposing said photochromic fluorescent protein moiety to said writing wavelength; irradiating said photochromic fluorescent protein moiety with a reading wavelength in an optical memory device; and detecting an output to determine whether said photochromic fluorescent protein moiety is in said first fluorescent state or second fluorescent state.

39. The method of claim 38 wherein, said first fluorescent state and said second fluorescent state are substantially stable at room temperature.

40. The method of claim 38, wherein said photochromic fluorescent protein moiety is an Aequorea-related photochromic fluorescent protein moiety.

41. The method of claim 40, wherein said second fluorescent state has a second excitation wavelength maximum, said second excitation wavelength maximum being longer than said first excitation wavelength maximum.

42. The optical memory device of claim 41, wherein excitation of said second fluorescent state at said second excitation wavelength maximum produces an intensity that is at least four times greater than said intensity of said first fluorescent state at second excitation wavelength maximum.

43. The method of claim 40, wherein said second fluorescent state has a second excitation wavelength maximum, said second excitation wavelength maximum being shorter than said first excitation wavelength maximum.

44. The method of claim 43, wherein detecting said output includes measuring an emission wavelength.

45. The method of claim 40, wherein said photochromic fluorescent protein moiety includes an amino acid substitution of T203.

46. The method of claim 40, wherein said photochromic fluorescent protein moiety includes an amino acid substitution T203F, T203Y, or T203S.

47. The method of claim 40, wherein said photochromic fluorescent protein moiety includes amino acid substitutions S65G/S72A/T203F, S65G/S72A/T203Y, or T203S/S205T.

48. The method of claim 38, wherein said photochromic fluorescent protein moiety is a single polypeptide.

49. The method of claim 38, wherein said medium is configured as a planar surface or a volume.

50. The method of claim 49, wherein said medium further includes polyacrylamide.

51. The method of claim 38, wherein each of said photochromic fluorescent protein moieties is individually addressable.

52. A method of improving a photochromic response of a photochromic fluorescent protein moiety, comprising:
growing a plate of bacteria containing a large number of mutations that express a photochromic fluorescent protein moiety to provide a plurality of colonies;
exposing said plurality of colonies to a first excitation wavelength and measuring an intensity of a resulting first emission I(A1) from said exposure to said first excitation wavelength of a colony;
exposing said plurality of colonies to a second excitation wavelength and measuring an intensity of a resulting second emission I(B1) from said exposure to said second excitation wavelength of a colony;
exposing said plurality of colonies to an isomerization wavelength;
exposing said plurality of colonies to said first excitation wavelength and measuring an intensity of a first emission I(A2) from said exposure to said first excitation wavelength for a colony;
exposing said plurality of colonies to said second excitation wavelength and measuring an intensity of a second emission I(B2) from said exposure to said second excitation wavelength for a colony;
determining said ratio of emission intensities from said colony before and after exposure to said isomerization wavelength; and
selecting said colony having improved photochromic response of said photochromic fluorescent protein moiety if said ratio of emission intensities is substantially different from an average ratio of emission intensities for said plurality of colonies.

53. The method of claim 52, wherein said photochromic fluorescent protein moiety is an Aequorea-related photochromic fluorescent protein moiety.

54. The method of claim 52, wherein said determining step includes calculating said ratio I(A2)/I(A1), I(B2)/I(B1), or I(A2)I(B1)/I(A1)I(B2).

55. The method of claim 52, further comprising exposing said plurality of colonies to an initial wavelength prior to said first exposing and measuring step.

56. The method of claim 52, wherein said exposing and measuring steps are performed with a digital imaging system.

57. The method of claim 52, further comprising picking up a portion of said colony having improved photochromic response of said photochromic fluorescent protein moiety.

58. The method of claim 57, wherein said picking up step is performed robotically.

59. An isolated nucleic acid sequence which encodes a photochromic fluorescent protein moiety capable of being converted from a first fluorescent state to a second fluorescent state by irradiation with a writing wavelength in an optical memory device, wherein said first fluorescent state has a first excitation wavelength maximum, said second fluorescent state has a second excitation wavelength maximum, excitation of said second fluorescent state at said second excitation wavelength maximum produces an intensity that is at least four times greater than said intensity of said first fluorescent state at said second excitation wavelength maximum.

60. The nucleic acid sequence of claim 59, wherein said first fluorescent state and said second fluorescent state are substantially stable at room temperature.

61. The nucleic acid sequence of claim 59, wherein said photochromic fluorescent protein moiety is an Aequorea-related photochromic fluorescent protein moiety.

62. The nucleic acid sequence of claim 61, wherein said photochromic fluorescent protein moiety is capable of being converted from said second fluorescent state to said first fluorescent state by irradiation with an erasing wavelength in an optical memory device.

63. The nucleic acid sequence of claim 61, said second excitation wavelength maximum is longer than said first excitation wavelength maximum.

64. The nucleic acid sequence of claim 61, said second excitation wavelength maximum is shorter than said first excitation wavelength maximum.

65. The nucleic acid sequence of claim 61, wherein said photochromic fluorescent protein moiety includes an amino acid substitution of T203.

66. The nucleic acid sequence of claim 61, wherein said photochromic fluorescent protein moiety includes an amino acid substitution T203F, T203Y, or T203S.

67. The nucleic acid sequence of claim 61, wherein said photochromic fluorescent protein moiety includes amino acid substitutions S65G/S72A/T203F, S65G/S72A/T203Y, or T203S/S205T.

68. An expression vector containing said nucleic acid sequence of claim 59.

69. An expression vector comprising expression control sequences operatively linked to a nucleic acid sequence coding for said expression of a photochromic fluorescent protein moiety capable of being converted from a first fluorescent state to a second fluorescent state by irradiation with a writing wavelength in an optical memory device, wherein said first fluorescent state has a first excitation wavelength maximum, said second fluorescent state has a second excitation wavelength maximum, excitation of said second fluorescent state at said second excitation wavelength maximum produces an intensity that is at least 4 times greater than said intensity of said first fluorescent state at said second excitation wavelength maximum.

70. The expression vector of claim 69, wherein said first fluorescent state and said second fluorescent state are substantially stable at room temperature.

71. The expression vector of claim 69, wherein said photochromic fluorescent protein moiety is an Aequorea-related photochromic fluorescent protein moiety.

72. The expression vector of claim 71, wherein said photochromic fluorescent protein moiety includes an amino acid substitution of T203.

73. The expression vector of claim 71, wherein said photochromic fluorescent protein moiety includes an amino acid substitution T203F, T203Y, or T203S.

74. The expression vector of claim 71, wherein said photochromic fluorescent protein moiety includes amino acid substitutions S65G/S72A/T203F, S65G/S72A/T203Y, or T203S/S205T.

75. The expression vector of claim 69, adapted for function in a prokaryotic cell.

76. The expression vector of claim 69, adapted for function in a eukaryotic cell.

77. A host cell transfected with an expression vector, comprising: an expression control sequence operatively linked to a sequence coding for said expression of a photochromic fluorescent protein moiety capable of being converted from a first fluorescent state to a second fluorescent state by irradiation with a writing wavelength in an optical memory device, wherein said first fluorescent state has a first excitation wavelength maximum, said second fluorescent state has a second excitation wavelength maximum, excitation of said second fluorescent state at said second excitation wavelength maximum produces an intensity that is at least four times greater than said intensity of said first fluorescent state at said second excitation wavelength maximum.

78. The host cell of claim 77, wherein said first fluorescent state and said second fluorescent state are substantially stable at room temperature.

79. The host cell of claim 77, wherein said photochromic fluorescent protein moiety is an Aequorea-related photochromic fluorescent protein moiety.

80. The host cell of claim 79, wherein said photochromic fluorescent protein moiety includes an amino acid substitution of T203.

81. The host cell of claim 79, wherein said photochromic fluorescent protein moiety includes an amino acid substitution T203F, T203Y, or T203S.

82. The host cell of claim 79, wherein said photochromic fluorescent protein moiety includes amino acid substitutions S65G/S72A/T203F, S65G/S72A/T203Y, or T203S/S205T.

83. The host cell of claim 77, wherein said cell is a prokaryote.

84. The host cell of claim 77, wherein said cell is *E. coli*.

85. The host cell of claim 77, wherein said cell is a eukaryotic cell.

86. The host cell of claim 85, wherein said cell is a yeast cell.

87. The host cell of claim 85, wherein said cell is a mammalian cell.

* * * * *